United States Patent [19]
Bouton

[11] Patent Number: 6,144,876
[45] Date of Patent: Nov. 7, 2000

[54] SCANNING A RADIATION SOURCE WITH A COUNT RATE OUTPUT DERIVED WITH A DYNAMIC WINDOW ANALYSIS

[75] Inventor: Chad E. Bouton, Dublin, Ohio

[73] Assignee: Neoprobe Corporation, Dublin, Ohio

[21] Appl. No.: 09/177,725

[22] Filed: Oct. 23, 1998

[51] Int. Cl.[7] ........................................... A61B 5/00
[52] U.S. Cl. ............................................. 600/436
[58] Field of Search .................... 600/407, 409, 600/424, 436, 437, 473, 476

[56] References Cited

U.S. PATENT DOCUMENTS

| | | |
|---|---|---|
| 4,782,840 | 11/1988 | Martin, Jr. et al. . |
| 4,801,803 | 1/1989 | Denen et al. . |
| 4,889,991 | 12/1989 | Ramsey et al. . |
| 4,893,013 | 1/1990 | Denen et al. . |
| 5,070,878 | 12/1991 | Denen . |
| 5,151,598 | 9/1992 | Denen . |
| 5,246,005 | 9/1993 | Carroll et al. . |
| 5,383,456 | 1/1995 | Arnold et al. . |
| 5,429,133 | 7/1995 | Thurston et al. . |
| 5,475,219 | 12/1995 | Olson . |
| 5,482,040 | 1/1996 | Martin, Jr. . |
| 5,732,704 | 3/1998 | Thurston et al. . |

OTHER PUBLICATIONS

Morton, et al. "Technical Details of Introperative Lymphatic Mapping for Early Stage Melanoma," *Arch. Surg.* 1992; 127:392–399.

Uren, et al, "Lymphoscintigraphy in High–Risk Melanoma of the Trunk: Pedicating Draining Node Groups, Defining Lypmhatic Channels and Locating the Sentinel Node," *J. Nucl Med* 1993; 34:1435–1440.

Guiliano et al, et al., "Lymphatic Mapping and Sentinel Lymphadenectomy for Breast Cancer," Annals of Surgery, vol. 220, No. 3:391–401, 1994, J.B. Lippincott Company.

Greenson, et al, "Identification of Occult Micrometastases in Pericolic Lymph Nodes of Dukes' B Colorectal Cancer Patients Using Monoclonal Antibodies against Cytokeratin and CC49," *Cancer* 1994; 73: 563–569.

Bertsch, et al, "Radioimmunoguided Surgery System Improves Survival for Patients with Recurrent Colorectal Cancer," *Surgery* 1995; 118: 643–639.

Arnold, et al, "Radioimmunoguided surgery in Primary Colorectal Carcinoma: An Intraoperative Prognostic Tool and Adjuvant to Traditional Staging," *American J. Surg.* 1995; 179: 315–318.

Scheebaum, et al, "The Significance of Intraoperative Periportal Lymph Node Metastasis Identification in Patients with Colorectal Carcinoma," *Cancer*, 1995; 75 2809–2817.

Cote, et al, "Intraoperative Detection of Occult Colon Cancer Micrometastases Using 125I–Radiolabeled Monoclonal Antibdy CC49," *Cancer* 1996; 77:613–620.

*Primary Examiner*—William E. Kamm
*Attorney, Agent, or Firm*—Mueller and Smith, LPA

[57] ABSTRACT

Count rate outputs of a probe-based radiation detection system are stabilized through the utilization of a dynamic window-based count analysis. Circular memory is utilized to record a sequence of segment count values. These values then are accessed and updated with respect to short scan intervals. The memory segments then are employed to develop a count sum over a count collection interval. That count sum is employed with algorithms adjusting the upper and lower edges of the dynamic window. A reported mean value, computed from the window upper edge or window lower edge, is utilized for creating a variable pitch output or for driving a bar graph. Background count and target count intervals are adjusted utilizing a data point predictive technique in combination with upper and lower time bounds.

39 Claims, 15 Drawing Sheets

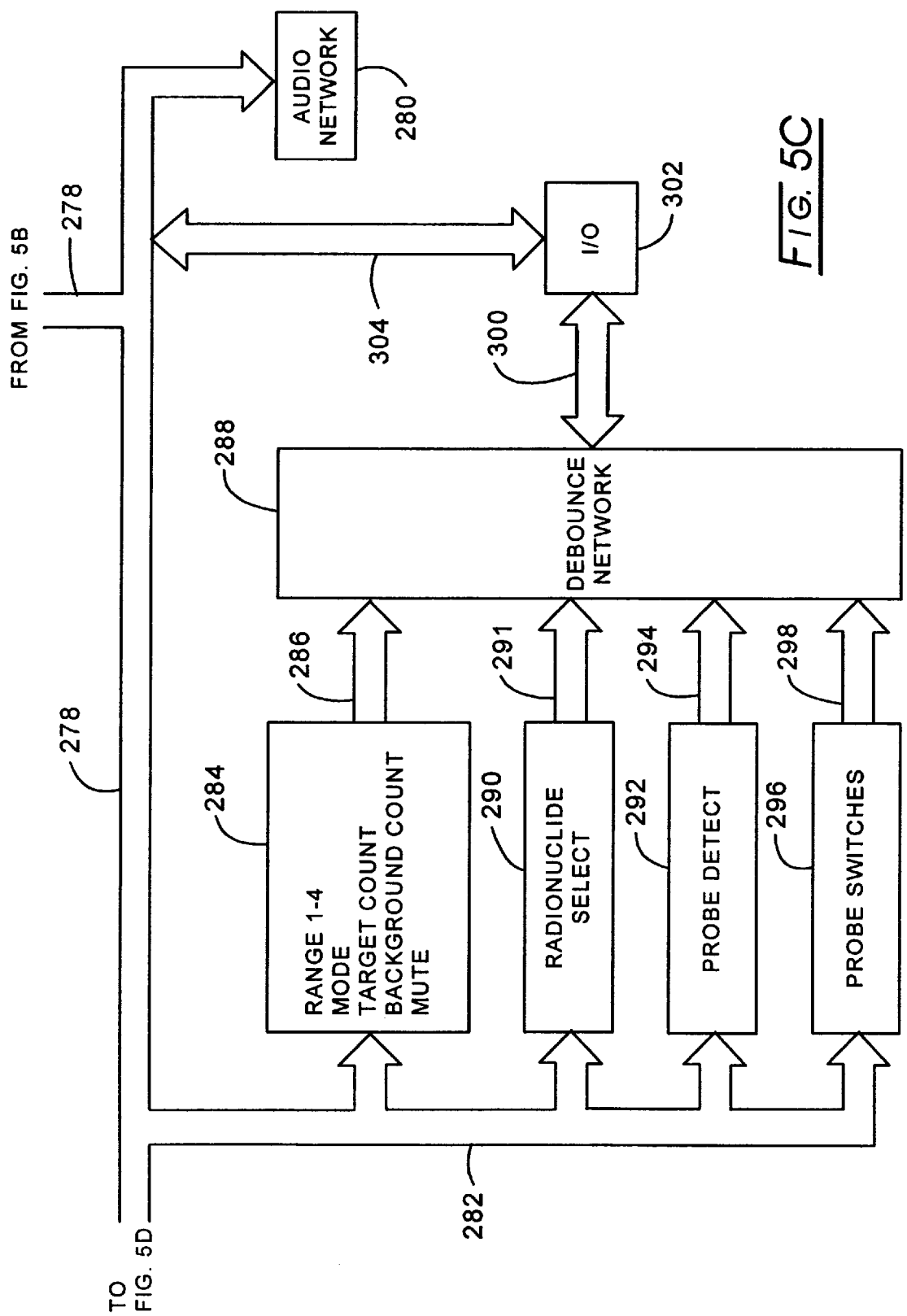

SCANNING A RADIATION SOURCE WITH A COUNT RATE OUTPUT DERIVED WITH A DYNAMIC WINDOW ANALYSIS

CROSS-REFERENCE TO RELATED APPLICATIONS

STATEMENT REGARDING FEDERALLY SPONSORED RESEARCH

Not applicable.

BACKGROUND OF THE INVENTION

Current and historical procedures for treatment of colon and rectal cancer generally have been based upon the natural history of tumor spread, and thence, upon operative and non-operative options available to the practitioner. Operative options generally have looked to the physical identification and surgical resection of tumor. A variety of techniques have been brought to bear in the art with the purpose of aiding the surgeon in detecting and localizing neoplastic tissue as part of this surgical procedure. ("Neoplastic tissue," for the present purposes, often is referred to as cancerous tissue, though malignant tumor and malignant tumor cells also are found in the terminology of the art. The term "neoplastic tissue" includes all of these.) A substantial amount of the effort which has been expended in seeking to aid the surgeon in the process of locating neoplastic tissue has been concerned with the utilization of radiolabeled antibody. For example, one technique includes the scintillation scanning of patients who have been injected with relatively high energy, e.g. $^{131}$I labeled antibodies. Such photoscanning scintigrams are difficult to interpret because of blood pool background radioactivity. Computer subtraction of radioactive blood pool agents and the use of two labeled antibodies (one specific for the tumor and one non-specific) have been attempted in an effort to enhance imaging. Nevertheless, such techniques have been found to provide little, if any, useful information to the surgeon, especially over and above the CAT scan, magnetic resonance imaging, and like traditional techniques. Typically, large tumor is readily located by the surgeon by visualization at the operating theater, and, in particular, through palpation, i.e. the feel of tumor as opposed to that of normal tissue. To achieve operative success, however, it is necessary for the surgeon to somehow locate "occult" tumor, i.e. tumor which cannot be found by the conventional surgical procedures of sight and feel. Failure to locate and remove such occult tumor generally will result in the continued growth of cancer in the patient, a condition often referred to as "recurrent" cancer. In general, conventional diagnostic techniques such as, for example, use of the classic gamma camera and the like, fail to find or locate occult tumor. As tumor sites become smaller, the radionuclide concentrations at a given site will tend to be lost, from an imaging standpoint, in the background where blood pool radiation necessarily is present in the patient.

In 1984, Martin, M.D., and Thurston, Ph.D., introduced a much improved method for locating, differentiating, and removing neoplasms. Such technique uses a radiolabeled antibody and a portable radiation detection probe which the surgeon may use intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure now is known as radioimmunoguided surgery (RIGS®) (RIGS being a registered trademark of Neoprobe Corporation of Dublin, Ohio). The RIGS system for surgery additionally is successful because of a recognition that tumor detection should be delayed until the blood pool background of the circulating radiolabeled antibody has had an opportunity to be cleared from the body. As a consequence, the photon emissions or radiation emitted at minute tumors, compared to surrounding tissue, becomes detectable in view of the proximity of the probe device to it. Fortuitously, the radiolabeled antibody is capable of remaining bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand-held probe positioned in close proximity with the tissue under investigation. The seminal patent concerned with the RIGS procedure is U.S. Pat. No. 4,782,840 by Martin and Thurston, entitled "Method for Locating, Differentiating, and Removing Neoplasms," issued Nov. 8, 1988, and assigned in common herewith, the disclosure of which is expressly incorporated herein by reference.

The important advances achieved through radioimmunoguided-surgery have been reported. See in this regard, the following publications:

(1) "Radioimmunoguided Surgery System Improves Survival for Patients with Recurrent Colorectal Cancer" Bertsch, et al., Surgery 1995; 118: 634–639.

(2) "Radioimmunoguided Surgery in Primary Colorectal Carcinoma: An Intraoperative Prognostic Tool and Adjuvant to Traditional Staging," Arnold, et al., American J. Surg. 1995; 179: 315–318.

(3) "The Significance of Intraoperative Periportal Lymph Node Metastasis Identification in Patients with Colorectal Carcinoma," Schneebaum, et al., Cancer 1995; 75: 2809–2817.

(4) "Identification of Occult Micrometastases in Pericolic Lymph Nodes of Dukes' B Colorectal Cancer Patients Using Monoclonal Antibodies against Cytokeratin and CC49," Greenson, et al., Cancer 1994; 73: 563–569.

(5) "Intraoperative Detection of Occult Colon Cancer Micrometastases Using $^{125}$I-Radiolabeled Monoclonal Antibody CC49," Cote, et al., Cancer 1996; 77: 613–620.

The radioimmunoguided surgical system instrumentation is comprised generally of two basic components, a hand-held probe, as described above, which is in electrical communication via a flexible cable with a control console. This control console is located within the operating room facility but out of the sterile field, while the hand-held probe and forward portions of its associated cable are located within that field. The hand-held radiation detecting probe is relatively small and performs in conjunction with a cadmium-zinc-telluride detector or crystal.

The hand-held probe and preamplification electronics mounted within it in support of the cadmium-zinc-telluride crystal have been the subject of extensive scientific development. Cadmium-zinc-telluride crystals are somewhat fragile and exhibit piezoelectric properties which, without rigorous accommodation, will produce deleterious noise phenomena and the like. Further, the crystal and its operatively associated preamplification function are called upon to detect necessarily very faint radiation. In this regard, only a very small amount of radioactive locator will be associated with minute, occult tumor. Thus, radiation emission count rates measured with the RIGS system are relatively low. Research activity concerning the above operational criteria is reflected in the following U.S. Patents.

U.S. Pat. No. 4,801,803 by Denen, Thurston and Ramsey, entitled "Detector and Localizer for Low Energy Radiation Emissions," issued Jan. 31, 1989.

U.S. Pat. No. 4,893,013 by Denen, Thurston and Ramsey, entitled "Detector and Localizer for Low Energy Radiation Emissions," issued Jan. 9, 1990.

U.S. Pat. No. 5,070,878 by Denen, entitled "Detector and Localizer for Low Energy Radiation Emissions," issued Dec. 10, 1991.

U.S. Pat. No. 5,151,598 by Denen, entitled "Detector and Localizer for Low Energy Radiation Emissions," issued Sep. 29, 1992.

To derive data representing the presence or absence of occult tumor, a microprocessor-driven complex system of analysis continuously works to statistically evaluate validated counts or gamma strikes to aurally apprise the surgeon of the presence or absence of occult neoplastic tissue. One algorithm under which the noted evaluation takes place is described in U.S. Pat. No. 4,889,991 by Ramsey and Thurston, entitled "Gamma Radiation Detector with Enhanced Signal Treatment," issued Dec. 26, 1989.

The RIGS system, not only having demonstrated its value in locating occult neoplastic tissue, also substantially aids the surgeon in determining the proper staging of the patient in accordance with the extent and severity of the disease. Such staging aids in determining the appropriate post-surgical treatment of patients. In this regard, an effective staging technique utilizing the RIGS system has been described wherein an R Number is determined in accordance with the formula:

$$R \text{ Number} = (n_1 \times E_1)_1 + (n_2 \times E_2)_2 + (n_3 \times E_3)_3 + (n_4 \times E_4)_4$$

wherein each subscript 1–4 represents an anatomic zone, staging of the patient being based upon the R Number determination. See generally, U.S. Pat. No. 5,482,040 by Martin, Jr., entitled "Biostaging of Adenocarcinomas Utilizing Radiolabeled Tumor-Associated Glycoprotein Antibodies," issued Jan. 9, 1996.

The RIGS system has been introduced into the field of laparoscopic surgery. See in this regard U.S. Pat. No. 5,429,133 by Thurston, et al., entitled: "Radiation Responsive Laparoscopic Instrument" issued Jul. 4, 1995 and U.S. Pat. No. 5,383,456 by Arnold and Thurston, entitled: "Radiation-Based Laparoscopic Method For Determining Treatment Modality" issued Jan. 24, 1995.

Cadmium telluride-based crystals, when employed in conjunction with the RIGS system perform admirably. Advantageously, higher purity levels for the compound crystals are not mandated in order to generate highly acceptable count-based outputs within an energy region of interest. Such performance, typically, is evaluated in conjunction with a multi-channel analyzer (MCA) relating counts with energy levels of interest. Where a sharp photopeak at the energy level of interest occurs which, in turn, is well spaced from regions of an MCA curve representing electrical noise, Compton scattering or the like, then windowing or thresholding out of such noise is a straightforward procedure. Cadmium telluride-based crystals achieve this excellent performance, inter alia, because they are used in conjunction with the radionuclide $^{125}$I which exhibits relatively low gamma energy (27–35 Kev). By contrast, the commonly employed $^{131}$I exhibits gamma energy of 360 Kev. The cadmium-zinc-telluride crystals employed with the RIGS system are, for the purposes of the instant discussion, considered to be "thin," i.e. having a thickness, d, of 2 mm. With the RIGS system, upon the occurrence of a photon event, a generation of carrier pairs generally will occur in a manner wherein holes are trapped at the grounded front face of the crystal. From that position they are immediately collected by the initial integration stage of a signal treatment system. The carrier electrons, traveling at a velocity which is about twelve times greater than the rate of hole migration, all move essentially the same distance, such that, even if they are trapped, they are trapped to the same degree, and the result is an excellently performing crystal detection system.

Over the recent past, practitioners have been desirous of utilizing instrumentation similar to the RIGS system in conjunction with higher energy radionuclides. In particular, a call has been made for a cadmium telluride-based hand-held probe device which is operable in conjunction with use of the radionuclide Technetium 99-m. The latter radionuclide exhibits a gamma energy level of, for example, 140 Kev. That value is somewhat excessive for the cadmium-telluride crystal architecture employed with the RIGS system. However, utilization of a hand-held probe with higher energy nuclides for the purpose of lymph system tracking is achieving importance.

The involvement of the lymph system in tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is importantly involved in participation with the blood vascular system in developing the immune response of the lymphocytes and other cells. Lymph flows within the system as a consequence of a variety of perceived mechanisms of organ and tissue dynamics. For certain cancers, metastasis, occurring in consequence of lymph drainage, will result in an initial location or positioning of neoplastic cells at certain lymph nodes typically deemed "regional nodes" within a pertinent lymph drainage basin. Some cancers, for example, melanomas, have been observed to exhibit variability in lymphatic drainage patterns emanating from different portions of the body. Other cancers, such as those encountered in the breast, will evidence somewhat more predictable nodal involvement. In designing forms of cancer disease management, therefore, efforts are directed to the identification of affected lymph nodes. For melanomas, it has been a more recent practice to identify the pertinent drainage basin or regional nodes along with an evaluation of the extent of lymph involvement with micrometastasis. A pre-surgical step undertaken in about 20% of investigational procedures concerning melanomas looks to the carrying out of a gamma camera generated form of lymphoscintigraphy which gives the clinician a gross two-dimensionally limited image, generally showing the tumor site injection of sulfur colloid labeled with Technetium 99-m ($^{99m}$Tc) and, spaced therefrom, a region of radioactivity at the pertinent regional lymph nodes. The latter information at least confirms the path of drainage and the location of the proper drainage basin. Regional nodes then are removed and submitted for pathology evaluation.

For cancers, such as breast cancer, the sites of lymph node involvement are commonly encountered at axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics, as opposed to therapy. In this regard, the combination of the presence and extent of metastasis to the axilla represents the single most important prognostic factor for the management of patients with breast cancer. See generally "Cancer, Principles and Practice of Oncology," vol. 1, 4th ed., DeVita, Jr., et al., chapter 40, Harris, et al., J.P. Lippincott Co., Philadephia, Pa. (1993).

The axilla is a triangular region bounded by the axillary vein superiorly, the laissimus dorsi laterally, and the serratus anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by investment or fatty tissue and visualization of them necessarily is limited. Such dissection will pose risks of cutting the long thoracic nerve, the thoracic-dorsal nerve, the nerve to the pectoralis major or the axillary vein. Morbidity may occur in some cases due to regional node removal, and patients are known to frequently discuss a numbing of the arm region following the procedure.

While this form of somewhat radical axillary lymph node dissection has been the conventional approach to determining nodal metastatic involvement, more recent data suggests that less radical axillary node evaluation procedures may generate equivalent information for staging and patient management, but with far more limited dissection and resultant trauma, as discussed below.

Patient management for staging purposes for the case of cutaneous melanoma is highly predicated upon determinations of lymph involvement. A number of factors are involved in the prognosis of the disease, including, inter alia, location, tumor thickness, level of invasion, growth patterns, and, of particular importance, the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial dialog has been carried on by investigators as to whether or not elective lymph node dissection, or lymphadenectomy, is an appropriate therapy. Elective lymphodenectomy has the major advantage of treating a nodal metastasis at a relatively early stage in its natural history when the tumor burden is low. On the other hand, such an approach may subject patients to surgery which would otherwise have been unnecessary. In particular, where patients exhibit a clinical Stage I level of the disease, there will be no nodal metastasis present, and no benefit then can be realized from regional lymphadenectomy.

Morton, et al., undertook an investigation of a procedure designed to identify that lymph node nearest the site of a melanoma and within the pertinent lymph drainage basin. Such a node, being on the most direct drainage pathway will present the most likely site of early metastasis and is referred to as the "sentinel node." Thus, by carrying out only a limited dissection, specific to this node and performing pathologic analysis of it, staging can be achieved without at least initial resort to more radical lymphadenectomy. With the approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively of blue color and readily identified. Thus, the sentinel draining lymph node of each primary melanoma is isolated and removed. By examining the sentinel nodes, for example by frozen section using routine hematoxylin-eosin histopathological techniques, as well as rapid immunohistochemical techniques, only those patients who have evidence of micrometastasis in the sentinel draining node are subject to subsequent lymphodenectomy. See generally, Morton D., Wen D-R, Wong J., et al. "Technical Details of Intraoperative Lymphatic Mapping for Early Stage Melanoma," *Arch. Surg.* 1992: 127:392–399; and R. F. Uren, et. al, "Lymphoscintigraphy in High-Risk Melanoma of the Trunk: Predicting Draining Node Groups, Defining Lymphatic Channels and Locating the Sentinel Node," *J. Nucl Med* 1993; 34:1435–1440.

The approach of Morton, et al., also has been undertaken to moderate the otherwise somewhat radical axillary lymph node dissection common in staging breast cancer. Through the utilization of the noted vital dyes, in conjunction with the lymph drainage system from primary breast tumor, less radical sentinel node based procedures may result in adequate axillary staging and regional control. With the procedure, in general, a vital blue dye is injected into the breast mass and surrounding breast parenchyma. Following a relatively short interval, a transverse incision is made just below the hair bearing region of the axilla. Blunt dissection is performed until a lymphatic tract or duct leading to a blue stained node is identified. The lymph duct, having a blue color, provides a guide path leading to the location of the most proximal lymph node and thus the sentinel node. This sentinel node is excised and evaluated. While the procedure calls for considerable surgical experience and talent associated with the delicate task of following the blue duct (a ruptured dye-carrying duct can be problematic), the ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes. See generally Guiliano, A. E.; Kirgan, B. M.; Guenther, J. M.; and Morton, D. L., "Lymphatic Mapping and Sentinel Lymphadenectomy for Breast Cancer," *Annals of Surgery*, vol. 220, no. 3: 391–401, 1994, J.B. Lippincott Company.

As a replacement for or an adjunct to the tracking of portions of the lymph system to locate a sentinel lymph node, practitioners have injected the noted sulfur colloid labeled with $^{99m}$Tc technician at the site of the lesion. Then, employing a hand-held radiation detecting probe, migration of the injectate along the lymph ducts to the sentinel node is carried out. Thurston, et al, in U.S. Pat. No. 5,732,704 entitled "Radiation Based Method for Locating and Differentiating Sentinel Nodes," issued Mar. 31, 1998, describe an improved technique for thus tracking a lymph duct and for utilizing a thresholding procedure three-dimensionally finding a radiolabeled sentinel lymph node with a hand-held probe.

As the use of radionuclides in the course of diagnostics and management of disease has expanded significantly over the past two decades, a concomitant need has arisen for instrumentation exhibiting a flexibility of use. Higher levels of computing power now are called for along with a flexibility or adaptability of performance. This calls for software driven equipment with software restructuring capabilities so as to readily convert equipment to new procedures and techniques which may employ a wide range of different radionuclides. Equipment improvements facilitating readout values and enhanced surgical data reporting are needed by practitioners both to ease the burden necessarily imposed within the surgical theatre and to evoke higher levels of measurement accuracy.

BRIEF SUMMARY OF THE INVENTION

The present invention is addressed to system, method and apparatus for detecting and locating sources of radiation, with particular applicability to interoperative lymphatic mapping (ILM) procedures. The scanning probe employed with the system performs with both an audible as well as visual perceptive output, which outputs exhibit output variations with corresponding vary count rate. A desirable stability is achieved in the readouts from the system through a signal processing approach which establishes a floating or dynamic window analysis of validated photon event counts. This floating window is defined between an upper edge, UT, and a lower edge, LT. The values of these window edges vary during the analysis in response to compiled count sum values. In general, the upper and lower edges will be spaced apart a value corresponding with about four standard deviations.

To compute these count sums, counts are collected over successive short scan intervals of 50 milliseconds and the count segments resulting therefrom are located in a succession of bins within a circular buffer memory. The count sum is generated as the sum of the memory segment count values of a certain number of the bins or segments of memory. Alteration of the floating window occurs when the count sum either exceeds its upper edge or falls below its lower edge. A reported mean, computed with respect to the window edge that is crossed, is developed for each scan interval which, in turn, is utilized to derive a mean count rate signal. The resulting perceptive output exhibits a desirable stability, particularly under conditions wherein the probe detector is in a direct confrontational geometry with a radiation source.

Numerical count rate values also are derived from the circular memory by accessing a number of memory segments representing a segment collection period of time. Updating this count rate value occurs, for example, each 500 milliseconds.

Another aspect of the invention provides for predictive generation of count values and readouts for a bar graph display, as well as the numerical display outputs for a targeted for target and background counts. With the approach, confidence levels and confidence intervals are employed to select the number of data points or count readings required to predict both the final count outcome and the time interval to reach it. The intervals developed with the approach are bounded, however, by a two second minimum time limit for data collection and a six second upper bound for data collection. The approach is advantageous when taking stationary count measurements, in many instances permitting the lessening of time required to achieve a background or target count.

Other objects of the invention will, in part, be obvious and will, in part, appear hereinafter. The invention, accordingly, comprises the method, system, and apparatus possessing the construction, combination of elements, arrangement of parts and steps which are exemplified in the following detailed description.

For a fuller understanding of the nature of the objects of the invention, reference should be made to the following detailed description taken in connection with the accompanying drawings.

BRIEF DESCRIPTION OF THE DRAWINGS

FIGS. 5A–5D combine as labeled thereon to provide a block diagram of the control system employed with the console shown in FIG. 1;

DETAILED DESCRIPTION OF THE INVENTION

Figure 1:
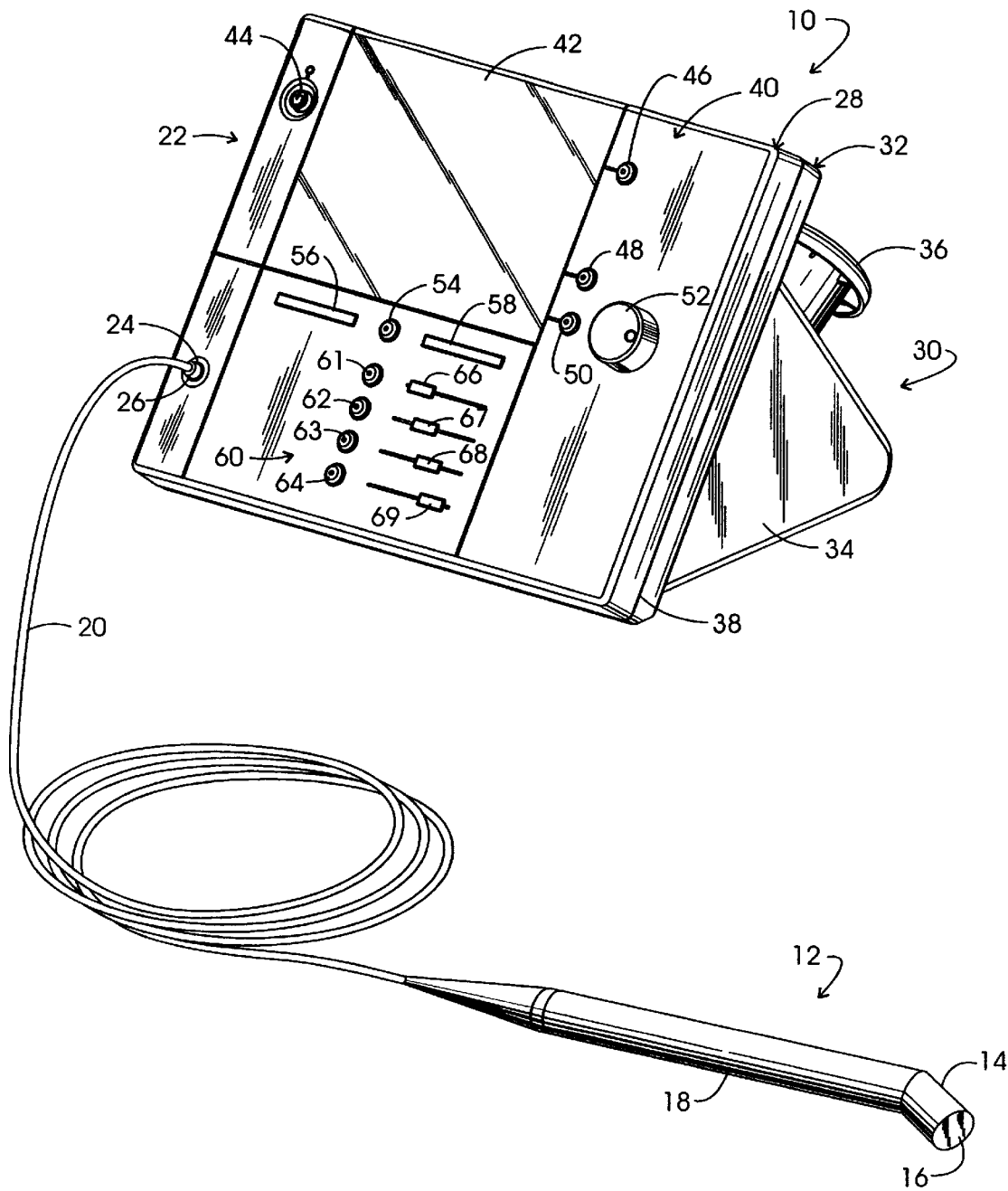
FIG. 1 is a perspective view of a system according to the invention including a console and associated hand-held probe.

Referring to FIG. 1, the system of the invention is represented generally at 10. System 10 performs in conjunction with a hand-held radiation detecting probe represented generally at 12. Probes, as at 12, are selected to perform in conjunction with any of a number of medical procedures and, thus, may assume a variety of configurations. Predominately for the present purposes, however, the probe 12 will perform in conjunction with radioimmunoguided surgery procedures (RIGS) wherein a cadmium telluride crystal, based detector performs in conjunction with a systemically injected locator which, for example, may be an antibody labeled with the radionuclide $^{125}$I. That procedure may utilize probes having a general structure as shown at 12 or probes intended for laparoscopic surveys or investigations. Another predominant use of the hand-held probes is involved with intraoperative lymphatic mapping (ILM). ILM procedures generally employ a higher energy radionuclide such as $^{99m}$Tc which is injected at the situs of a lesion, and the probes then are utilized to locate that node within a lymph drainage basin designated as a "sentinel" node. Probes as at 12, may assume a variety of configurations. In this regard where cadmium telluride crystal detectors are employed, then different operational modes for these crystals are utilized based upon the radionuclide energy involved. In general, probes as at 12, will incorporate a forward structure as at 14 containing a crystal mount for retaining a detector crystal such as cadmium telluride. The forward face of such crystal typically will be in very close proximity but spaced from a radiation transmissive window as at 16. Extending rearwardly from the forward structure 14 is a hand-grippable handle portion 18 which may support signal treatment circuitry such as preamplifiers and the like. A pulsed output is generated from this preamplification function in response to photon events or interactions with the detector crystal, and such pulsed outputs are conveyed, typically, by a flexible cable or suitable transmission assembly as at 20 to a control assembly represented generally at 22. In this regard, a connector 24 at the outward end of flexible cable 20 is connected in electrical association with the corresponding connector 26 of the assembly 22.

Control assembly 22 is seen to be formed having a forward housing component 28 of generally rectangular peripheral design. Forward component 28 is joined with a rear housing component represented generally at 30. This component 30 includes a rectangular forward support portion 32 which meets with the rearward edge of forward housing component 28. Additionally, the rear housing component 30 includes a rearward support portion 34 having a somewhat triangular cross section and which is integrally molded with the forward support portion 32. This provides for the support of the forward housing component 28 at a convenient, rearwardly tilted orientation as shown. Preferably, the amount of such tilt is about 57°. This angularity facilitates manual switch actuation and adjustment by the user as well as promotes the readability of a readout display. Inasmuch as the control assembly 22 is powered from a conventional A.C. line voltage source, a cord wrap fixture 36 is molded within the rearward support portion 34. In general, the forward housing component 28 and rear housing component 30 are injection molded of an ABS/Polycarbonate blend which is resistant to the solvents and disinfectants typically encountered in the medical field. It may be noted that a parting line or joint 38 is present at the juncture or union of forward housing component 28 and the rectangular forward support portion 32 of rear housing component 30.

The forward face of the control assembly 22 is represented generally at 40 and is seen to support a relatively large readout main display window 42. Window 42 is formed of a polycarbonate that will make a strong weld joint with the ABS/Polycarbonate forward housing component 28. The view through the display window 42 is enhanced by an anti-glare coating, and an ultraviolet cured coating is employed with the window 42 to improve its scratch resistance. All front housing transparent components are ultrasonically welded in place to assure that liquids will not breach the enclosure. Between the window 42 and the forward housing component 28 is a graphics overlay which contains informational symbols and functions to provide organization to multi-segmented character forming light emitting diodes (LEDs) mounted just rearwardly of the forward face 40, including window 42. Such LEDs serve to provide a very bright and readily discerned visual readout perceived by the surgeon working at the somewhat remote sterile field of a surgical theatre.

The most predominately utilized manual control components are mounted at the forward face 40 of the control assembly 22. In this regard, where switches are employed, they are formed of a silastic button style configuration, for example a material sold under the trade designation "Santoprene" marketed by Scientific Molding Corp., of Somerset, Wis. Looking to the switch assemblies, an on/off switch is provided at 44 at one side of the display window 42. Adjacent the opposite side of display window 42 is a "target" switch 46. When the momentary on target switch 46 is pressed and immediately released, a "target check" procedure representing a two second count by the probe 12 is carried out. Where the switch 46 is held on or actuated for at least one second, a "target count" procedure is carried out for an interval of six seconds. These latter count intervals are exclusive to the operation of system 10 in a RIGS mode. Next below the switch 46 is a background count switch 48. Switch 48 is used in a RIGS mode of operation for the development of statistically significant thresholds, counting for background occurring utilizing probe 12 at a predetermined location during and just prior to surgery. Next below the background count switch 48 is a mute switch 50. During some procedures, the practitioner will wish to avoid the audio output of the system with the exception of aural feedbacks for switch actuation. Accordingly, those former sounds may be muted by actuating switch 50 which will perform in all operational modes including RIGS and ILM. The level of audio output is controlled by a volume encoder shown as a knob 52. Encoder 52 provides a coded input of from one to 128 positions such that control software can provide a broad variety of audio output volumes depending upon the mode employed with the system 10.

Below the center of display window 42 is a mode selection switch 54. Actuation of switch 54 alternately elects one of the two predominate operational modes of system 10, i.e., a RIGS procedure, which will result in the illumination of an elongate rectangular output display at 56. This RIGS mode of operation additionally is referred to as "binary pitch" operation. Alternate actuation of switch 54 will elect an ILM operational mode with the illumination of an elongate rectangular output display 58. The latter mode of operation also is referred to as a "dynamic pitch" operation. For the latter operational mode, in view of the high energy level and larger quantities of radionuclide material employed, count rate ranges may be elected by the operator. Accordingly, an array of range switches represented generally at 60 are mounted at the forward face 40. The momentary push switches are shown at 61–64 and respectively correspond with ranges of 0–100 CPS, 0–1000 CPS, 0–10000 CPS, and 0–50000 CPS. With the election of a given range by actuation of one of the switches 61–64, a corresponding range indicator, shown respectively at 66–69, is illuminated. In general, each of the ranges will incorporate an initial threshold level below which no audible or visual cueing will occur. That range, for example, may be 2% of the maximum count value for the given range. The ranges also may be restricted by a background count initiated at switch 48.

Figure 2:
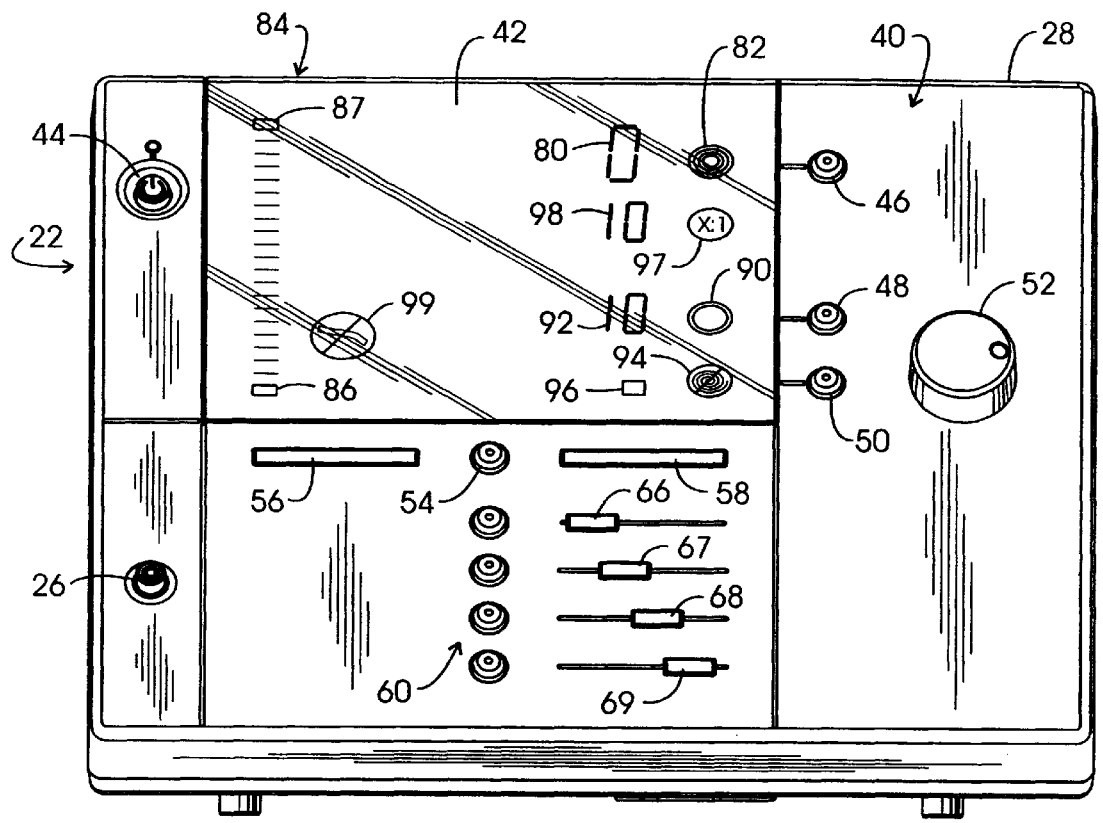
FIG. 2 is a front view of the console shown in FIG. 1.

Referring to FIG. 2, the forward housing component 28 again is revealed. However, shown at the display window 42 are visual readouts which are generated in conjunction with the operation of system 10. To facilitate the ease of operation of the system 10, on a worldwide basis, icon imagery or graphical labels are employed, inter alia, in conjunction with the switches 46, 48 and 50. Colors also are used to indicate relationships between data items and to enhance understanding of the displays. Further, the visual indicators have the ability to be flashed or energized intermittently in order to draw attention to a given data or procedural item. The indicators also are operated in a mainer to help differentiate between a period when the data item is being acquired by system 10 and the period when the acquired data then is being displayed. In this regard, a flashing indicator generally means that the associated data item is being updated as a result of an operator action.

Running count rate data is published at the window 42 with a large bright LED derived segmented character representation which is located generally horizontally from the target switch 46. This numeric readout is shown at 80 in FIG. 2. During the operation of the system 10 when the target counts are not underway in consequence of the actuation of switch 46, the count rate data published at 80 is updated each ½ second. However, where the practitioner actuates the target switch 46, for example, in a RIGS mode of operation to derive a target check, then the numeric data at 80 disappears in favor of dashes and an icon assembly containing an icon 82 with the shape of an international target is intermittently energized or flashed for the two second collection period. This same flashing occurs in conjunction for example, with the six second target count data collection occurring during the RIGS mode of operation. Following the data collection interval, then the target count or target check count rate information is published utilizing the numeric output 80 and is sustained at the window 42 for the relatively short display interval, for example of five seconds. Following that display interval, then the conventional ½ second updated count rate data is published in conjunction with the readout indicia as at 80. At the opposite side of the display window 42 there is provided a sixteen segment bar graph represented in general at 84 and having bottom and top (first and last) illuminated segments shown respectively at 86 and 87. To appraise the practitioner of the amount of time remaining for the collection of data associated with the actuation of target switch 46, the LED implemented sixteen segment bar graph 84 will "fill" or illuminate segment by segment from bottom segment 86 toward top segment 87 during the predetermined data collection intervals. Thus, the surgeon will be aware of how much additional time the probe 12 should be retained in count position. When the system is operated in an ILM mode, this same form of information is provided, however, it is tempered or improved with respect to a number of data points collected representing an adequate degree of confidence. This follows, for example, in the ILM mode because of the relatively larger count rates involved, permitting a rapid development of confidence levels. Thus, with the exception of lower and upper bounds in data collection times, at higher count rates the segments of the bar graph 84 will fill for this ILM procedure on an expedited basis.

Actuation of the background switch 48 while system 10 is in a RIGS mode will cause the carrying out of a six second background count evaluation. During the progress of this background counting, a background icon assembly 90 represented as a dual ring is energized on an intermittent or flashing basis. While the six second counting ensues, the bar graph 84 will correspondingly "fill" from lower segment 86 to upper segment 87 in correspondence with that set six seconds. The background value will be published as numerical indicia as at 92 at the termination of the interval. With the completion of background computation, the system 10 will compute a ratio of background count rate to the currently measured count rate and publish it as at 98 along with a ratio indicia (97) intermediate icons 82 and 96 and indicia 80 and 92. During the ILM mode, the bar graph 84 publishes count rates over the earlier noted default threshold or, when utilized, over a background count ratio, the segments of the bar graph 84 are energized from first to last in accordance with the difference between either threshold or background and the current level of count. Such display also reflects the range selected from the switch array 60. The audio output of the system 10 when operating in the noted ILM mode, also provides a varying pitch or frequency output which is compressed between the lower threshold or background count and the upper frequency limit.

Actuating the mute switch 50 in the course of a procedure provides for the energization of a mute icon assembly represented at 94. The icon 94 so displayed represents a sound wave pattern with a slash positioned across it. Also illuminated during the course of a procedure at one of six rectangular positions across the bottom of display window 42 is an illuminated indication of the type of radionuclide utilized. The ILM mode indicator, depicting $^{99m}$Tc, is shown in FIG. 2 at 96. The system 10 defaults to this indicator upon actuation of switch 54 for one mode. Correspondingly, another actuation of mode switch 54 will illuminate a similar indicator at the opposite side of window 42 showing a $^{125}$I radionuclide utilization. Four other radionuclides may be selected with the system by actuation of a switch (not shown) mounted at the rear housing component 30 (FIG. 1). Radionuclides which may be elected are, for example: $^{57}$Co, $^{111}$In, $^{18}$f and $^{131}$I, and at such time as the system 10 is activated, but probe 12 is not connected properly or is inoperative, a probe defect icon as at 99 is energized at the lower left side of display window 42.

The software driven control features of system 10 perform in conjunction with a standard bus architecture referred to as "PC/104." This standard bus approach is desirable in view of a small form factor (3.55 inch×3.25 inch) which reduces crowding within the control assembly 22 enclosure. Control architecture including a CPU board, an I/O board, a DSP board and a unique pulse detector module (PDM) are mounted to the PC/104 mother board or backplane and are located outwardly from but parallel therewith. The forwardly directed surface of this backplane functions, inter alia, to support the LED based circuits associated with display 42, as well as the range displays 66–69 and the mode selector displays 56 and 58. That face of the board also cooperates with the manually actuated components of the switches at forward face 40.

Figure 3:
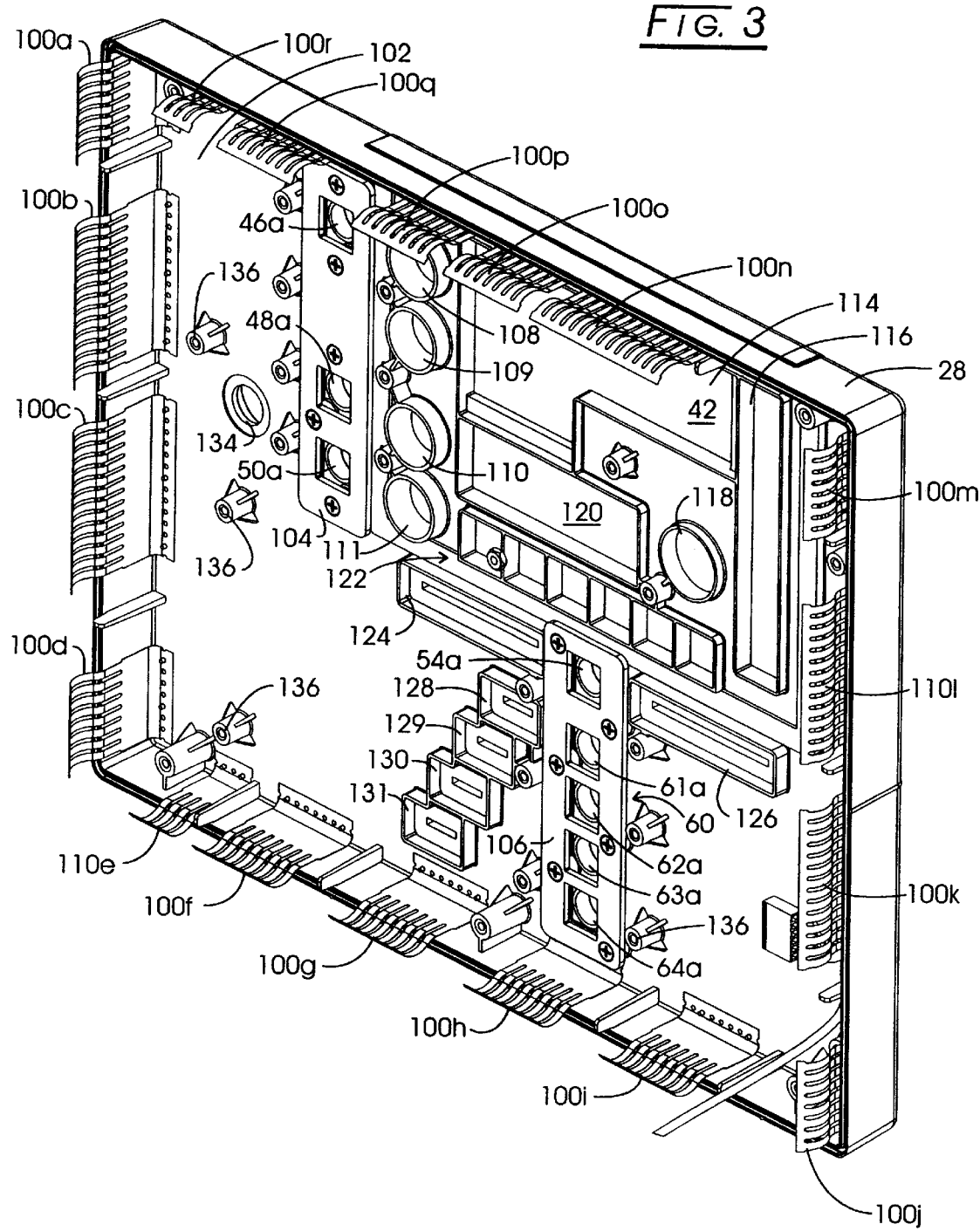
FIG. 3 is a perspective view looking into the internal side of a forward housing component of the console shown in FIG. 1.

Looking to FIG. 3, the rearward side of forward housing component 28 is revealed as it appears before the positioning of the noted backplane and its associated and supported components. In FIG. 3, a tongue-in-groove form of edge connection as described in FIG. 1 at parting line 38 is revealed with the same numeration. To provide for EMI filtering, the entire interior surfaces of both the forward housing component 28 and rear housing component 30 are coated with an aluminum containing conductive material which is vacuum deposited. To preserve the integrity of the shield at the union between components 28 and 30 as at parting line 38, the interior surface of forward housing component 28 supports a plurality of EMI gaskets 100a–100r formed, for example, of beryllium-copper spring-like material. When the forward housing component 28 is mated with rear forward support portion 32 of rear housing 30, the gaskets 100a–100r complete the EMI security feature. Switches 46, 48 and 50 are formed having silastic cup-shaped cover assemblies which extend through openings within the forward face 40. As they extend through that forward face, the outwardly flared inward edges of these switch covers are compressibly retained against the rear surface 102 of forward housing component 28. To secure them in this compressed arrangement, a metal switch-plate 104 is secured against them using machine screws. In similar fashion, cup-shaped silastic switch cover assemblies 54a and 61a–64a are retained at the back surface 102 by a metal switch-plate 106. In general, when the practitioner depresses one of the elastomeric cup-shaped switch cover assemblies, contact is made with corresponding conductive switching elements which are supported upon the forward face of the noted backplane. The minimization of discrete wiring thus achieved is a substantial advantage in fabrication of the control apparatus 22.

To avoid cross talk or light scatter, for the most part, the LED illuminated display features including icons, indicators and numerical indicia as well as bar graph 84 are formed as assemblies with baffles isolating the light emitting components. In this regard, the circular icons including target icon 82, the ratio icon (97) background icon 96 and mute icon 94 are retained within respective light restricting cylindrical baffle channels or wells 108–111. In similar fashion, the numerical indicia representing general count rate as at 80 and the ratio valuation 98 just below it are retained within a rectangularly shaped light restricting channel 114. Adjacent to light restricting channel or baffle 114 is another vertically oriented rectangular light restricting channel 116 at which the multi-segment bar graph 84 is located. Adjacent to channel 116 is another light restricting cylindrical baffle or well 118 which surrounds an LED array functioning to illuminate icon 99 representing that probe 12 is inoperative. Below the light restricting channel 114 and baffle 118 is another rectangular light restricting channel 120 which is employed with background count rate numerical indicia published by LED formations mounted upon the noted backplane. Next below the channel 120 is a horizontal sequence of six light restricting channels or baffles of generally square configuration which function to confine light extending to a display showing the earlier noted radionuclide identifications including, for example, that for $^{99m}$Tc shown at 96 in FIG. 2. This array is represented generally at 122. Below the array of light restrictors 122 are two elongate rectangular light baffle channels 124 and 126 which surround LED illuminator arrays providing the mode indicator illumination described at 58 and 56 in FIG. 2. Next extending below the channel 124 is a sequence of four rectangular channels 128–131 which baffle and confine light from light emitting diode arrays serving to illuminate the respective range indicators 66–69 described in FIG. 2. Access for the volume encoder knob 52 as seen in FIG. 2 is provided through an opening 134 which, as with all the above described components, cooperates with the backplane. Additionally shown on the drawing are a plurality of standoffs, some of which are identified at 136, which are employed for purposes of securing the backplane or mother board to this forward housing component 28.

Figure 4:
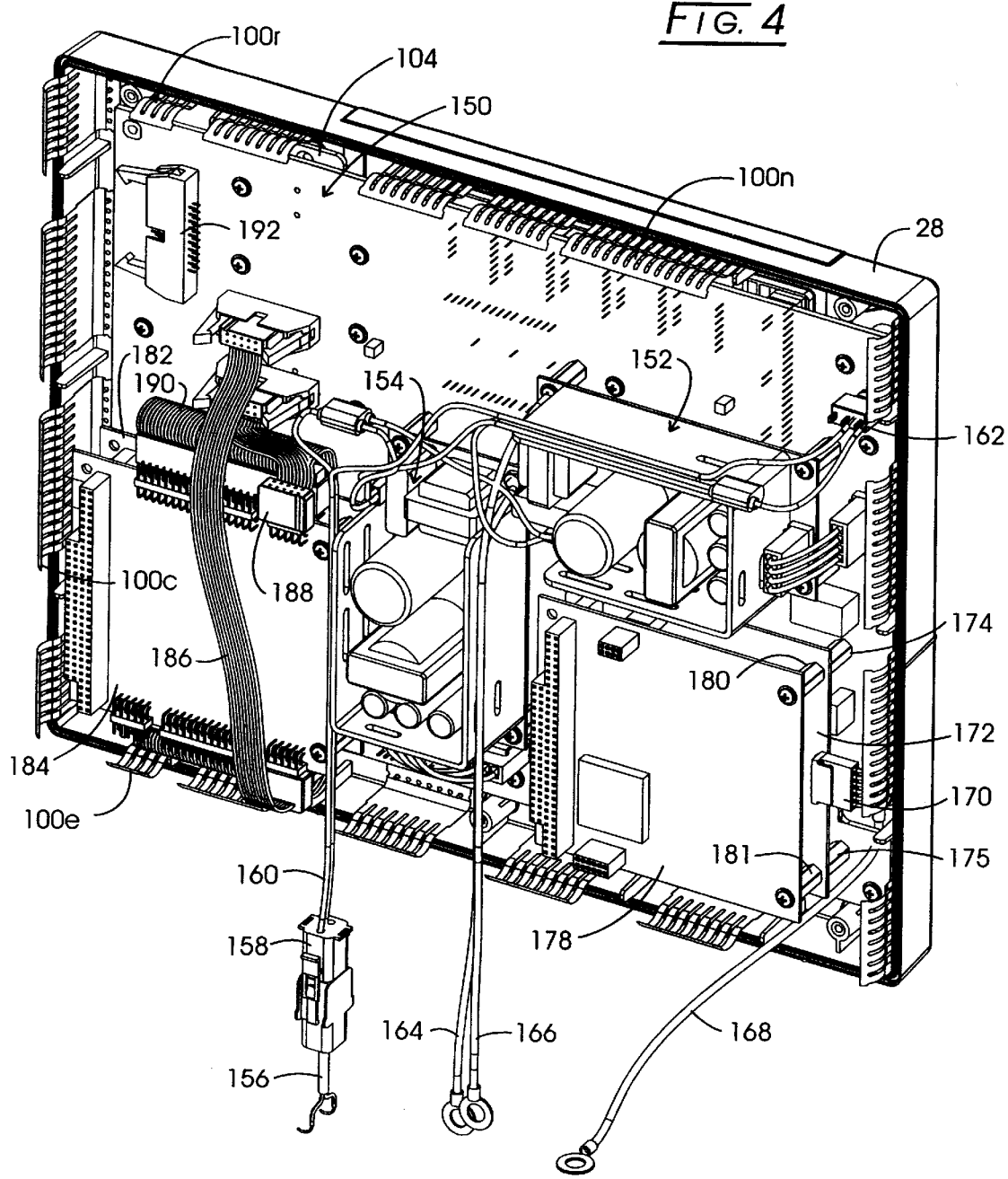
FIG. 4 is a perspective view of the forward housing component of FIG. 3 with the inclusion of power supplies and circuit boards.

Turning to FIG. 4, the forward housing component 28 again is shown but with the installation of the noted backplane with standard PC/104 bus and associated backplane mounted components. In the figure, the backplane is represented in general at 150 and is seen to have a thin rectangular structural aspect dimensioned to be positioned against the rearward structure of component 28 as described in connection with FIG. 3. Mounted upon the rearward face of backplane 150 is a generally horizontally disposed open-framed 12 volt power supply represented generally at 152, and vertically oriented in adjacency therewith is a 5 volt open-framed power supply represented generally at 154. Each of these power supplies are electrically connected with an a.c. utility input introduced from the rear housing component 30 (FIG. 1). That a.c. input is directed via a cable seen in FIG. 4 at 156 which extends through an a.c. line filter 158 and thence, as represented at 160 to power supplies 152 and 154. Additionally coupled with this input and power supply circuit is the power, on/off switch 44 terminal at 162 which is supported on the backplane 150.

Positioned in parallel stacked relationship and in electrical communication with the bus architecture of the backplane 150 are four rectangularly-shaped circuit boards. As before, by being associated with this standardized bus structure, substantial numbers of lead connections are eliminated, and the more ideal data transfer interconnections of a bus system are realized. Further, such structuring provides independent upgradability of each circuit board under the /104 standards criteria. Power converter grounds are provided from the rear of the assembly 22 from flexible cables as seen at 164 and 166, while in similar fashion, probe 12 ground input is provided from the rearward component 30 of assembly 22 by a flexible cable connection as represented at 168. This connection 168 extends to a probe dedicated terminal 170 which, in turn, is electrically associated with the input connector 26 (FIG. 1). Terminal 170 is seen in electrical connection with a printed circuit board 172 upon which is formed a signal treatment circuit. In this regard, the board is generally referred to as a pulse detector module board (PDM). Mounted to the rearward face of backplane 150 by standoffs, two of which are revealed at 174 and 175 and multiple pin connectors (not shown) the signal treatment carried out at the board 172 is one treating the pulse output from a preamplification stage contained within the probe 12 itself. Connected within the bus architecture and parallel adjacency with PDM board 172 is a printed circuit board 178. As before, mechanical connection is made utilizing standoffs, two of which are seen at 180 and 181 and multiple pin connectors. Board 178 supports a digital signal processor circuit (DSP). The DSP component utilized with board 178 is a type TMS 320 series by Texas Instruments, Inc. of Dallas, Tex., and the board employing that DSP is a Starburst type 104C31 marketed by Nova, Inc., of Cincinnati, Ohio. On the opposite side of the 5 volt power supply 154, there is provided an input/output circuit board 182 which provides a 48 line I/O function performing in conjunction with the standardized bus architecture. The board 182 may be provided, for example, as a part number EMM-DIO-PO by Diamond Systems, Inc., of Palo Alto, Calif. Mounted over and in parallel adjacency with the board 182 is a central processing unit board 184 (CPU). The CPU board 184 may be provided, for example, as a model 4 DXi marketed by Ampro, Inc., of San Jose, Calif. The CPU function at board 184 is a 133 MHz 486DX based PC/104 board with onboard programming of flash memory, floppy/IDE interface, serial ports, parallel port and serial boot loader capability. Software and onboard programming capabilities enables the software of system 10 to be upgraded without removing board 184 from the control assembly 22. Cables associated with the CPU function at board 184 are seen at 186 and 188 while I/O cable is seen at 190. Not shown in the figure but mounted for access at the rear housing component 30 is an axillary board carrying a manually actuable switch for selecting any of the earlier six noted radionuclide mode setups. Additionally, a data (serial) port is provided which is electrically associated with the central processor control at board 184. Further included but not shown in the drawing is a cooling fan mounted at rear housing component 30. A connector is shown at 192 mounted upon backplane 150. It may be used in conjunction with the noted auxiliary board.

Figure 5A:
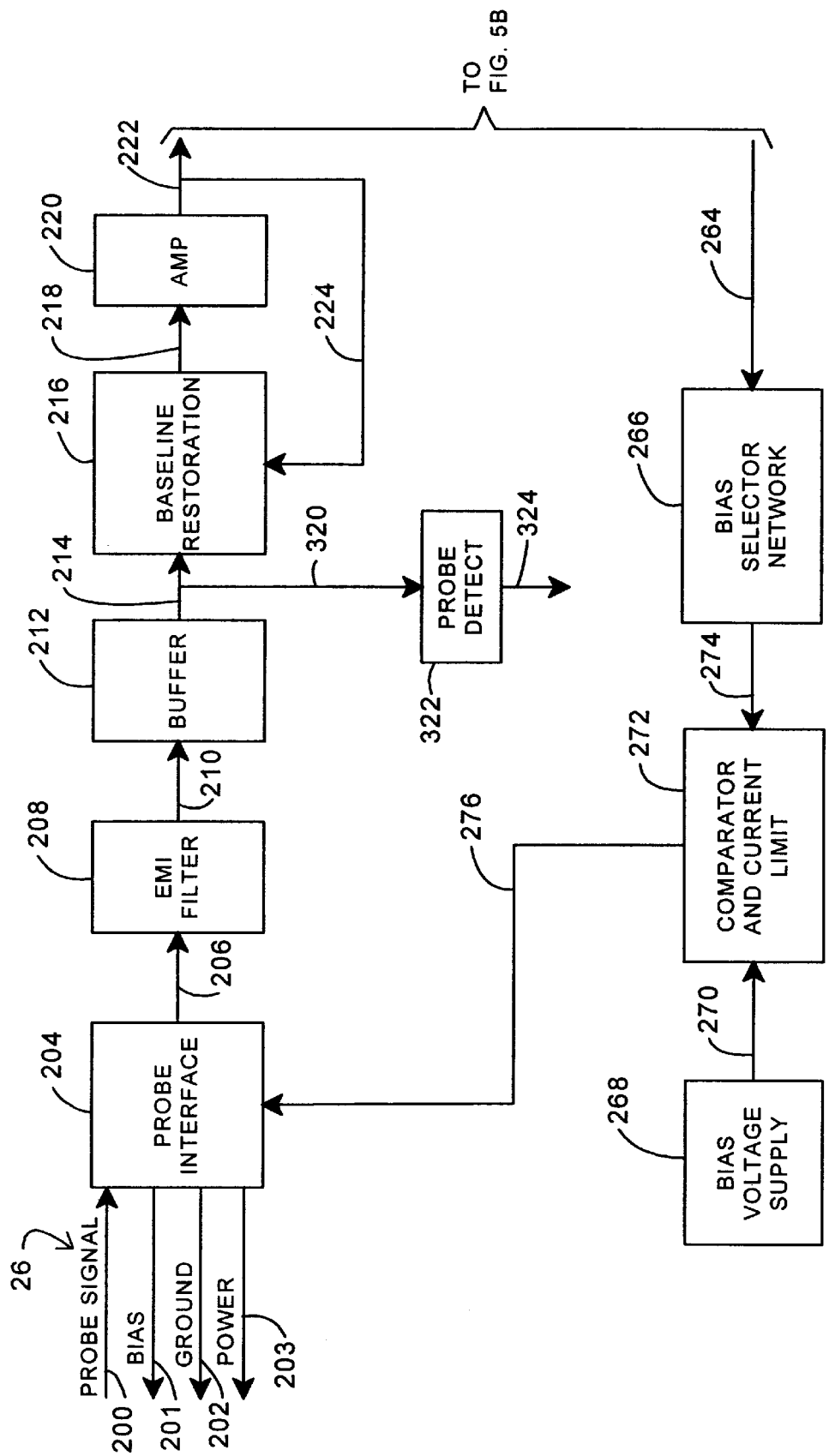

FIGS. 5A–5D are block diagrammatic representation of the control system. These FIGS. 5A–5D should be considered in an orientation established by the labeling thereon. Referring to FIG. 5A, connector 26 is represented in general as looking to four components of the interface of control apparatus 22 with the probe 12. In this regard, as represented at line 200, a data signal present as a pulsed output will be carried by a line represented at 200. From the control circuitry, a voltage bias is provided at line 201 for the operation of tie detector component of the probe 12.

Similarly, ground as represented at line 202 is carried to the probe 12 detector component and, as represented at line 203, circuit power, for example at +12 volts, is supplied to the probe 12. Lines 200–203 are shown in operative association with a probe interface circuit function represented at block 204. The pulsed output as provided at line 200 generally will exhibit a narrowness which, in terms of time, will be of two to seven microsecond duration at 10% of its height. From the interface function 204, the pulse signal or pulse train is introduced, as represented at arrow 206, to an EMI filter network represented at 208. Stage 208 functions to remove very high frequency EMI noise and has no operational effect upon the pulsed output. From the filtering function 208, as represented at arrow 210 and block 212, the pulsed output is buffered. In general, the buffer stage 212 is implemented as a unity gain operational amplifier. The thus buffered signal, as represented at arrow 214, then is submitted to a baseline restoration network represented at block 216. In general, the function at block 216 is one incorporating an a.c. coupling capacitor. At very high pulse rates, without baseline correction, the resultant pulse train tends to degrade, falling below the lower threshold of a window circuit which is later encountered. To correct for this phenomenon, a time-dependent base line restoration network is provided which derives a soft clamp retaining the output of the coupling capacitor at, for example, ground in the absence of a pulse. This avoids the noted downward drift of the pulse train. The advantage of this form of baseline restoration resides in its immunity to any distortion of pulse height. Thus, probes of different operational pulse widths can be employed with the system. From the baseline restoration at block 216, as represented at arrow 218 and block 220, the signal then is amplified. The amplification stage represented at block 220 is one, for example, providing a gain of 2.5. The resultant amplified signal then is present at arrow 222. That output is tapped as represented at arrow 224 to provide the noted time dependent input to the baseline restoration network 216.

Figure 5B:
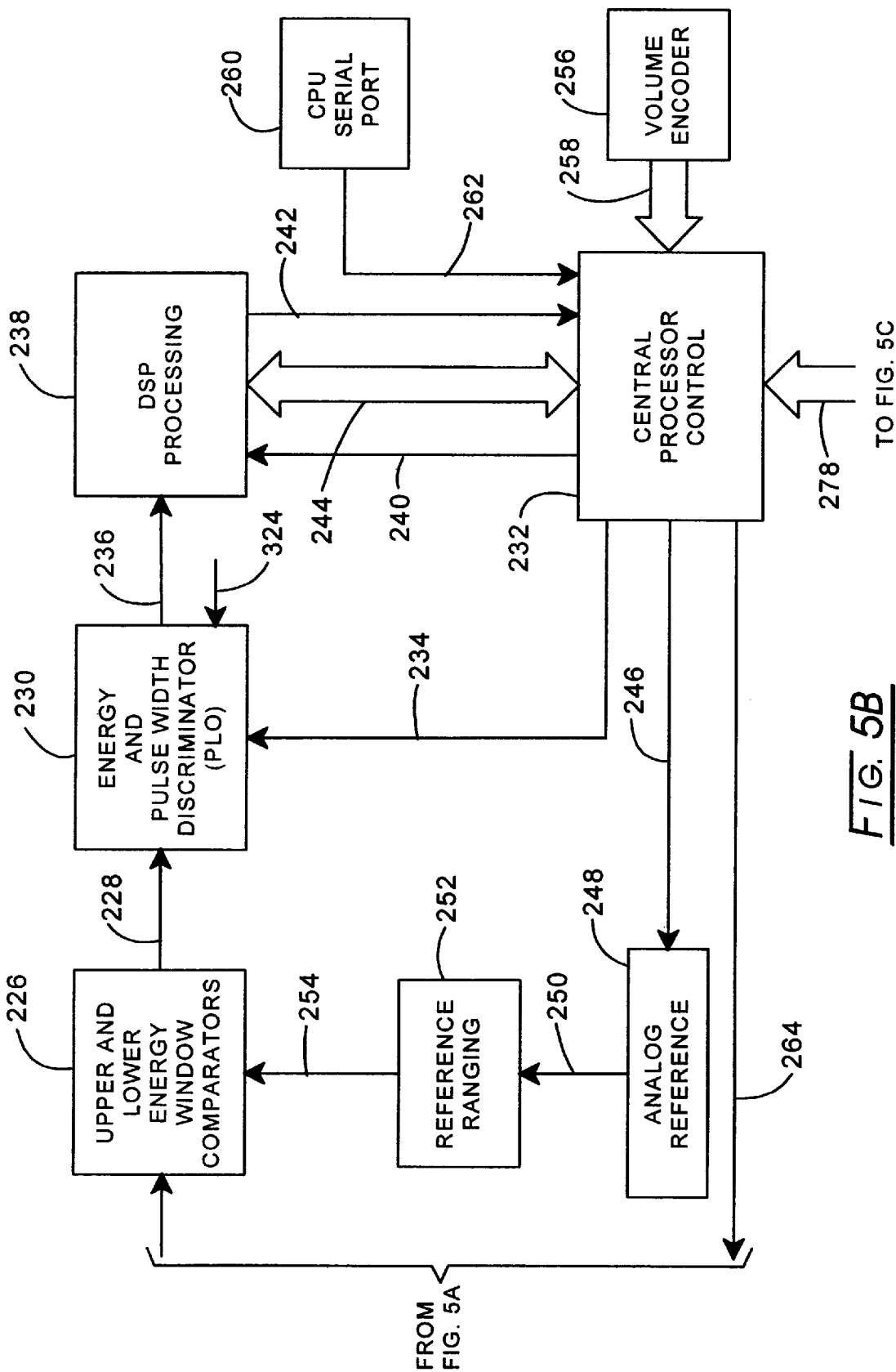

Looking additionally to FIG. 5B, arrow 222 reappears as it directs the amplified probe signal to a validation network including upper limit and lower threshold energy comparators as represented at block 226. The network 226 identifies those pulses which are above a lower threshold reference which, for convenience, is provided at ground and which exceed a reference level representing an upper limit. The resulting data then is presented, as represented at arrow 228, to an energy and pulse width discriminator function represented at block 230. In general, the function 230 is implemented with a programmable logic device (PLD). This logic device validates the pulses which are below the upper limit and above the lower threshold of the window function represented at block 226. Additionally, the function at block 230 times the pulse identification at the lower threshold of the window comparator function at block 226 to determine pulse width. Experience with the system 10 has shown that valid pulses will exhibit a pulse width at that lower threshold of less than about 12 microseconds. Lengthier pulse widths statistically will represent noise. Thus, a logical ANDing activity occurs at the function 230 requiring pulse validation with respect to the windowing function represented at block 226 and with respect to pulse width as evaluated from the lower threshold comparator of the windowing network. The PLD device implementing function 230 performs under the supervision of a central processor control or central processing unit (CPU) as represented at block 232 and arrow 234.

Upon being validated, a pulsed output then is transferred to a digital signal processing activity (DSP) as represented by arrow 236 and block 238. This DSP network has been described in conjunction with DSP circuit board 178 in FIG. 4. The DSP function 238 is slaved to or controlled by the central processor control 232 as represented at arrow 240 and provides signal information thereto as represented at arrow 242. Data transfer with respect to the PC/104 bus architecture between the DSP function at block 238 and the central processing function at block 232 is represented by the bus arrow 244. In general, the DSP function 238 develops count rate data in accordance with a variety of algorithms which additionally determine the statistical significance of count rates with respect to background count rate and the generation of count rate data which is displayed at display window 42.

As represented by arrow 246 and block 248, the central processor function 232 also develops an analog reference voltage level which is employed to provide the reference level for the upper limit and lower threshold comparators at the window function represented at block 226. A digital-to-analog function, which is made available at the DSP board function represented at block 238, is utilized for this purpose. However, in the interest of clarity, the function is shown as a separate block. By providing a control over the analog reference level from the central processor and DSP 238, that processor can react to the selection of a particular radionuclide by the user and automatically apply the proper window references. In this regard, the analog output from the function represented at block 248 is directed as represented at arrow 250 to a reference ranging network represented at block 252. The ranging function at block 252 asserts a precision with respect to the applied analog reference level by performance with a precision reference voltage developed at the PDM circuit board 172 described in conjunction with FIG. 4. The appropriately perfected references then are supplied to the upper and lower energy window comparators as represented by arrow 254.

The central processor control function 232 also receives volume data selected by user manipulation of knob 52 (FIG. 1) from an input/output circuit 302 via the bus architecture. The encoding function is represented in FIG. 5C at block 256, while bus-related communication is represented at bus arrow 258. Serial port communication also is provided at the central processor control function 232 as represented at block 260 and bidirectional arrow 262. Such communication with the central processor control function 232 permits the reprogramming of system 10 to accommodate future requirements. Control, as represented at arrow 264 also is provided from the central processor control function 232 to a bias selector network represented at block 266 in FIG. 5A. The selector network 266 responds to a digital input to effect the application of a particular bias voltage level at line 201 for presentation to a particular probe as at 12. In general, that bias level will be selected in response to the election by the user of a particular radionuclide. In this regard, it may be recalled that a radionuclide selector switch is provided with the control assembly 22 at its rear housing component 30, and selection of the two most predominating radionuclides is made at switch 54 located at the forward face 40 of assembly 22. These bias levels may be the same for given or selected ones of the radionuclides or may be different depending upon the probe and associated detector architecture. To provide an initial bias voltage supply, an unregulated relatively higher voltage supply as provided at the PDM circuit board 172 is represented in FIG. 5A at block 268. As represented at arrow 270, that bias voltage is delivered to a comparator and current limit network represented at block 272. The comparator network 272 responds to a selection signal from the network represented at block 266 as represented at arrow 274 to develop a predetermined bias level for delivery to the probe interface function represented at block 204 as, in turn, represented at arrow 276.

Referring to FIGS. 5B and 5C, the PC/104 bus architecture is represented at bus arrows 244 and 278 as being in control-asserting communication with a variety of switching and user perception associated outputs. As represented at block 280, an audio network is provided which may be a type ES1688 marketed by ESS Technology, Inc. That highly integrated device interfaces directly with the bus architecture of system 10. The network function represented at block 280 includes a speaker and amplifier, the speaker being mounted at the bottom of the rear housing component 30. FIG. 5C identifies the switching functions and probe detection features of the system 10, as they perform in conjunction with the bus 278. In this regard, the bus arrow 278 is seen to branch at 282 for communication with the switches described in connection with FIG. 1. For instance, the range switches 61–64 are associated with the bus; mode switch 54 also is so associated with the bus; target count switch 46 is coupled into the bus architecture; background count switch 48 also is so connected and mute switch 50 is associated with bus 282. These switch functions are represented at block 284 and they further are associated within the bus architecture, as represented at bus component arrow 286, with a switch debounce network represented block 288. The radionuclide select switching function shown at block 290 mounted at the rear housing component 30 also is functionally associated with the bus architecture as represented at 282. Through that bus architecture shown as at bus component 291 the bus system provides an input through debounce network 288. System 10 also provides a signal output in the event that probe 12 is inoperative, for example, not being properly connected with the control assembly 22. That probe detect function is represented at block 322 in FIG. 5A in association with arrows 214 and 320. A probe signal is delivered, as represented by arrow 324 to PLD network 230 (FIG. 5B and thence into the bus architecture. The probe detect signal associated with bus component 282 is shown to extend through bus component 294 to the debounce network 288. Finally, the probe 12 may be configured having one or more switches mounted upon its handle. Typically, those switches will emulate target switch 46 and/or background switch 48. Such a switching feature is represented at block 296 in association with the bus architecture 282 and through bus component 298 with the debounce network 288. Debounce network 288 is associated through the bus architecture as represented at bus arrows 300 and 278 with an input/output (I/O) network 302. Network 302 additionally is seen associated with the bus architecture bus component 278. The IO network 302 is mounted upon the I/O board 182 described in connection with FIG. 4.

Figure 5D:
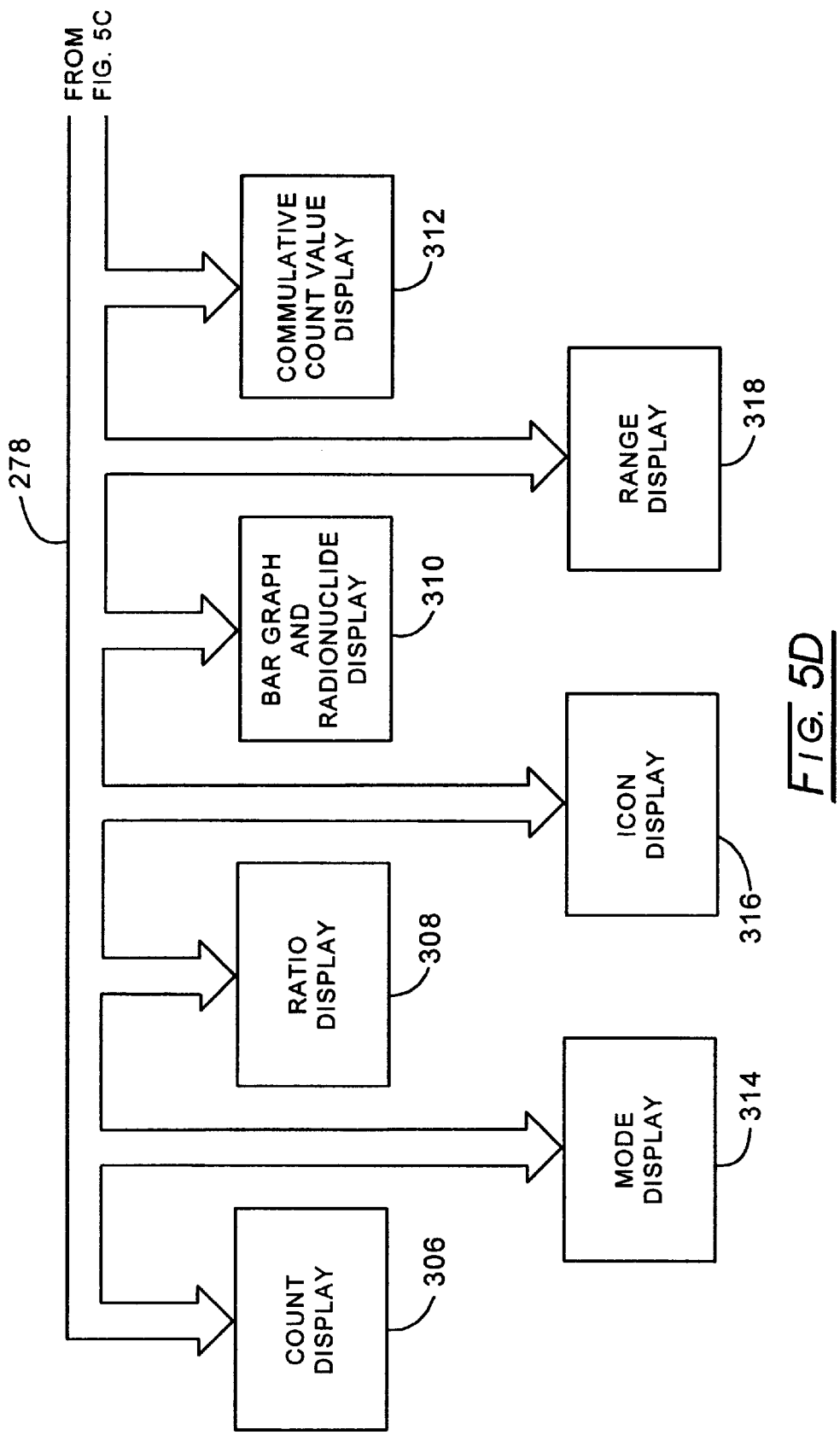

Looking to FIG. 5D, the bus architecture component 278 is seen to continue its association with a variety of display features. These displays are illuminated with LED arrays under control ultimately of the central processor control function represented at block 232. One count display, such as that represented at 92 in FIG. 2 associated with the background count, is represented in FIG. 5D at block 306. Positioned upwardly from that display is a ratio value display which is represented at block 308. In general, the ratio display is provided in conjunction with the target count development which, it may be recalled, requires a six second count reading when system 10 is operating under the RIGS mode. No such ratio display is provided during the shorter duration target check associated with switch 46. The bar graph and radionuclide display is represented at block 310 to facilitate user perception, the lowermost and uppermost segments of the 16 segment bar code display are illuminated in a different color than the other segments, for example, they may be illuminated in an amber color while the intermediate segments are illuminated in a green coloration. A "cumulative" count value display is that associated with the output described at 80 in FIG. 2 and is represented herein at block 312. A mode display is represented at block 314. That mode display is one of those visually perceptible outputs at 56 or 58 as shown in FIG. 2. The icon displays including icons representing target count, ratio, background count, mute and probe detect are represented at block 316. Finally, a range display as associated with perceptible display outputs 66–69 is represented at block 318. In general, all of these LED arrays are supported from the forward surface of the backplane or mother board 150 (FIG. 4).

Figure 6A:
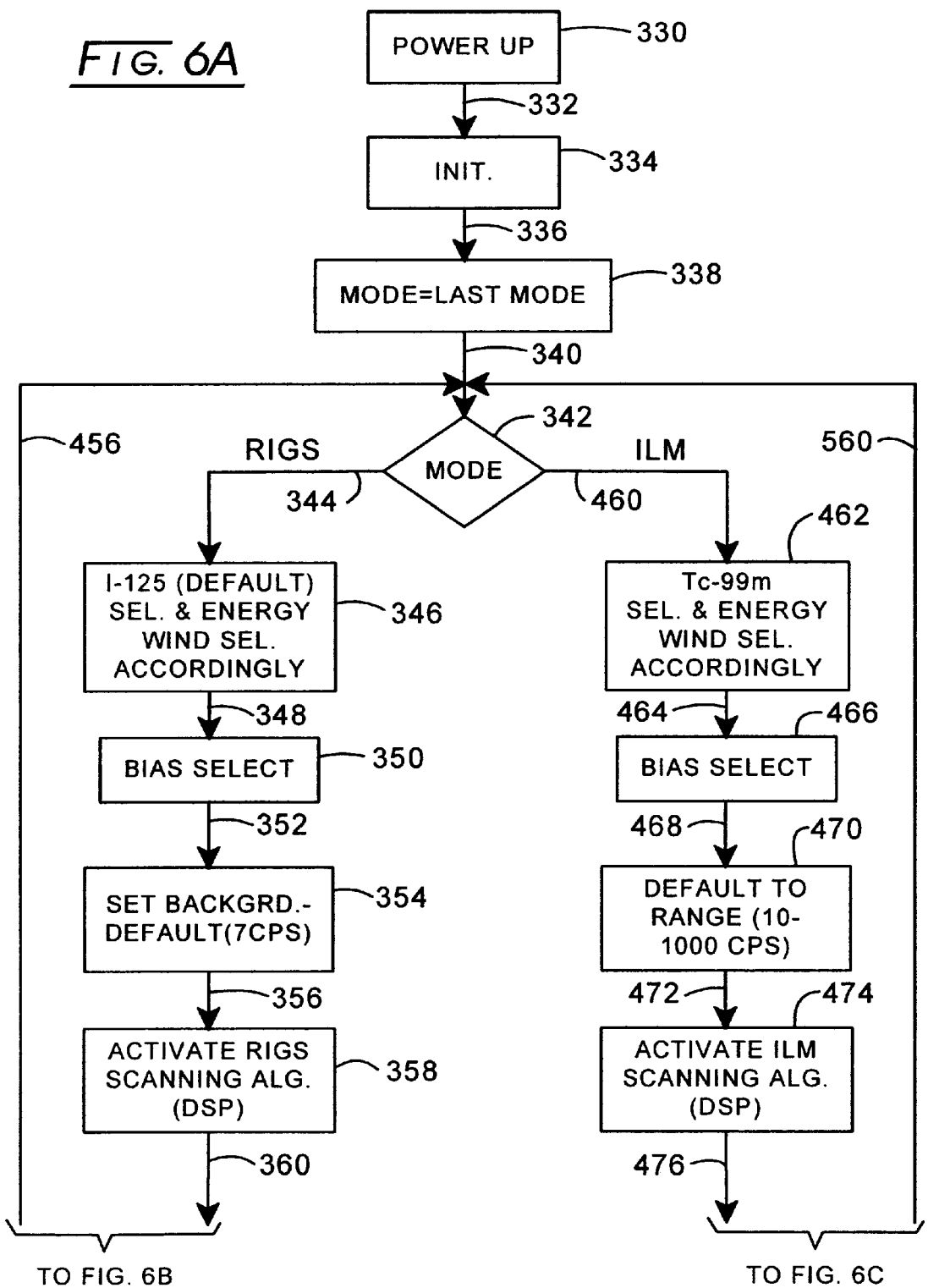
FIGS. 6A–6C combine as labeled thereon to provide a flow chart describing the main program utilized by a control processor control of the console shown in FIG. 1.
Figure 6B:
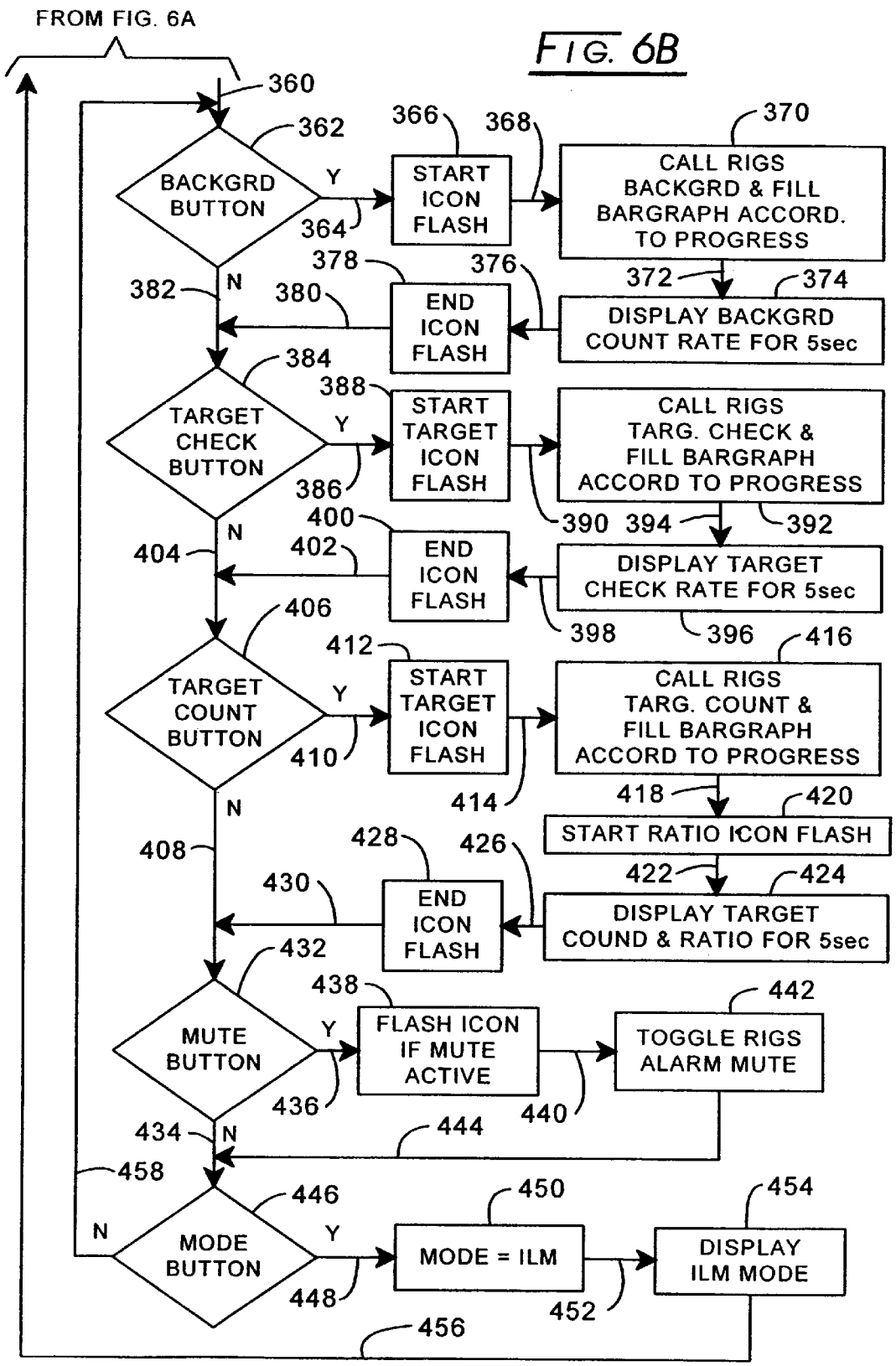
Figure 6C:
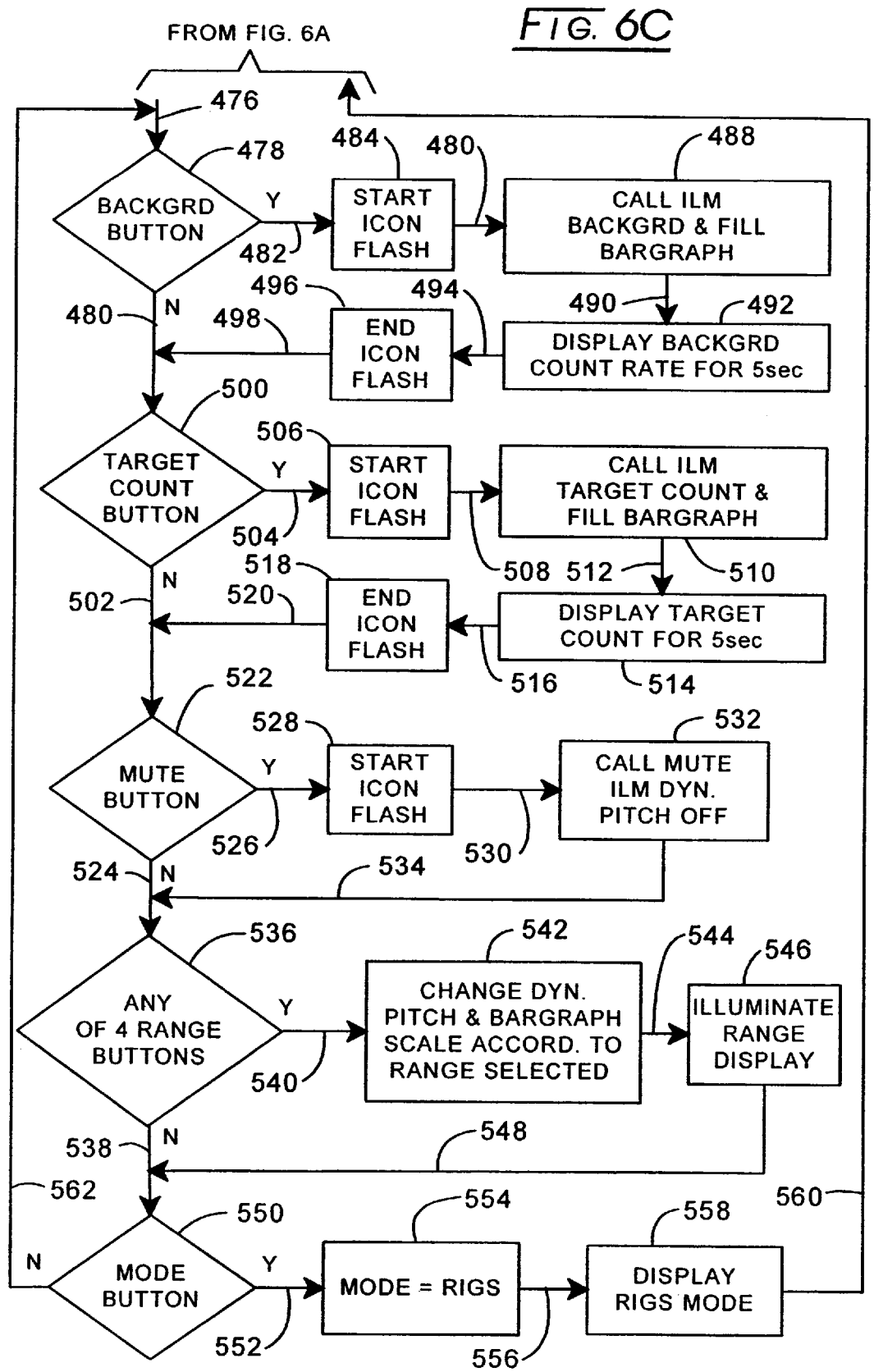

Referring to FIGS. 6A–6C, a flow chart illustrating the main program executed by central processor control 232 as it performs in conjunction with DSP processing function 238 is revealed. The program commences as represented at block 530 with the carrying out of power up. In general, this occurs with the actuation of power switch 44. Then, as represented at line 532 and block 534 initialization procedures are carried out. For these procedures, default values are acquired. If the probe detect function 322 indicates a non-connected probe 12, then 99 is illuminated at display window 42. The program then continues as represented at line 536 and block 538 to default to the last operational mode utilized. In this regard, the two modes concerned at this juncture are the ILM mode and the RIGS mode. For the present flow chart, only those modes are considered. The program then continues as represented at line 540 and block 542 to enter the mode elected. Should the user have changed modes by actuation of switch 54, then that election will be present at this juncture in the program. For either mode, probe 12 is "scanned" along a region of interest. For either For either mode, probe 12 is "scanned" along a region of interest. The term is intended to encompass all probe movement and stationary positioning occurring during a collection of photon event data. For the instant demonstration, assuming a RIGS mode has been elected, then the program proceeds as represented at line 544. This RIGS mode also is referred to as a "binary pitch" mode of operation. The RIGS mode of operation commences as represented at block 546 with a default selection of the radionuclide $^{125}$I, and the computer selects the reference values for the upper limit and lower threshold of the energy window function 226 accordingly. Continuing as represented at line 548 and block 550, the program then elects an appropriate bias for the selected radionuclide, in this case $^{125}$I. This is done by submitting information to the bias selector network 266. Then, as represented at line 552 and block 554, a background default value of seven counts per second is acquired. This background count generally will be altered by the practitioner with the actuation of the background count switch or button 48. Following the election of the default background value, as represented at line 556 and block 558, the RIGS scanning algorithm is activated. This algorithm is executed at the DSP processing function 238. In general, that algorithm utilizes a circular buffer form of temporary memory which is employed to collect validated photon event pulses in 50 millisecond time segment intervals. A statistically significant threshold valuation is computed with respect to each of predetermined combinations of those memory segments and where computed count rates exceed the computed threshold values in a predetermined number, then an aurally perceptive output is generated to apprise the surgeon that the probe 12 window 16 is adjacent tissue having a high probability of tumor involvement. After an initial threshold passage at a first statistical evaluation involving three standard deviations, the algorithm reverts to evaluations at a lowered standard deviation value. When the threshold is not met, on predetermined numbers of occasions, then the aural cueing is terminated and the higher statistical valuation is reasserted. The algorithm further retrieves count data from the circular buffer memory on a half second interval basis to publish a "cumulative" count rate as earlier described at 80 in connection with FIG. 2. The program then continues as represented at line 560 which line reappears in FIG. 6B. Looking to that figure, line 560 is seen directed to the decision block 562 wherein a query is made as to whether the background button or switch 48 has been actuated. In the event that it has, then as represented at line 564 and block 566, the background icon, as described at 96 in FIG. 2, is caused to commence to flash or be energized intermittently. Then, as represented at line 568 and block 570, the program calls the RIGS background program which carries out a count evaluation for a fixed interval of six seconds and, as that six seconds occurs, the bar graph 84 is proportionately filled from its lower segment 86 to its upper segment 87. This gives the surgeon a visual cue as to where in the background evaluation process the system 10 is. The program then continues as represented at line 572 and block 574 to carry out a displaying of the background count rate value at the location shown at 92 in FIG. 2 for a limited interval of five seconds. During the flashing of the background icon, the background count rate location as at 92 provides a dashed display. The program then continues, as represented at line 576 and block 578, to end the background icon flashing and, as represented at lines 580 and 582, to continue the program. Line 582 represents a program path followed additionally where the inquiry posed at block 562 results in a negative determination. The program then continues to the query posed at block 584 wherein a determination is made as to whether the target switch or button 46 has been depressed and immediately released to cause commencement of a target check count evaluation. This target check evaluation calls for the collection of count data at a given location for a shorter interval of two seconds. In the event that the target check button condition is at hand, then as represented at line 586 and block 588, the target icon as described at 82 in FIG. 2 is caused to be energized intermittently, i.e. to flash. Then, as represented at line 590 and block 592 the RIGS target check program is called which, as noted, carries out a two second count evaluation. During this two second count evaluation, the bar graph 84 segments are filled from first to last, i.e., from segment 86 to segment 87. This, as before, provides the surgeon with a visual cue as to the status of this procedure. The program then continues as represented at line 594 and block 596 to provide for the display of the count rate developed from the target check procedure at location 80 in window 42. This display is only for a limited interval of five seconds. During the two second interval of collecting data, dashes are displayed at location 80. The program then continues, as represented at line 598 and block 600, wherein the icon flashing is terminated at the end of the five second display. As before, the program then continues as represented at lines 602 and 604. Line 604 additionally represents a continuation of the program where the query posed at block 584 results in a negative determination. Line 604 is seen to extend to block 606. At block 606 a query is posed as to whether a target count button actuation at switch 46 has been carried out. This occurs when the operator holds button 46 down for a one second interval. In the event of a negative determination, the program continues as represented at line 608. Where an affirmative determination is made with respect to the query at block 606, then, as represented at line 610 and block 612, the target icon as described at 82 in FIG. 2 is intermittently energized or caused to flash. Then, as represented at line 614 and block 616, the RIGS target count program is called to carry out a six second target count. During this six seconds, the segments of the bar graph 84 are illuminated from first to last or filled so as to apprise the surgeon as to the progress of this procedure. The program then continues as represented at line 618 and block 620 to cause a ratio icon as described at 78 in FIG. 2 to flash. Then, as represented at line 622 and block 624, the target count rate is displayed at location 80 as described in FIG. 2. Additionally, the ratio of the target count to the current background count is computed and displayed at location 76 at display window 42. These displays of target count and ratio values are transitory, being limited to an interval of 5 seconds. The program then continues as represented at line 626 and block 628 wherein at the termination of the five second display interval, the energization of the two pertinent icons is terminated. The program then continues as represented at lines 630 and 608. Line 608 is seen directed to the query posed at block 632 wherein a determination is made as to whether the mute button 48 has been pressed. In the event that it has not, then the program continues as represented at line 634. In the event of an affirmative determination with respect to the query posed at block 632, then the program continues as represented at line 636 and block 638. If the mute condition is active, then a mute icon described at 94 in FIG. 2 is energized intermittently or flashed. The program then continues as represented at line 640 and block 642 wherein the RIGS alarm mute function is toggled. In this regard, an aural feedback representing the mere pushing of a switch button remains active in the system. However, all RIGS aural cueing is suppressed. The program then continues as represented at lines 644 and 634. Lines 634 is seen directed to the query posed at block 646 wherein a determination is made as to whether the mode selection switch or button 54 has been pressed. In the event that it has, then, as represented at line 648 and block 650, the mode of system 10 is altered to an ILM mode and, as represented at line 652 and block 654, the ILM mode display 58 is illuminated. As represented at line 656 which continues into FIG. 6A the program loops to line 540 to commence an ILM mode of performance. In the event of a negative determination with respect to the query posed at block 646, then as represented at line 658 the program loops to line 560 to evaluate which actuation on the part of the operator.

Returning to FIG. 6A, where the program enters into an ILM or "dynamic pitch" mode of operation, as discussed above in connection with block 542, then as represented at line 660 and block 662, the radionuclide $^{99m}$Tc is elected and the program selects the appropriate reference levels for the upper limit and lower threshold energy windowing function 226. The program then continues, as represented at line 664 and block 666, to select the appropriate bias at the bias selector network 266 for the radionuclide at hand. Then, as represented at line 668 and block 670 default is made to an initial range of 10 to 1000 counts per second. The program then continues as represented at line 672 and block 674 to activate the ILM scanning algorithm, which algorithm is performed at the DSP processing function 238. In general, this algorithm employs a floating window form of analysis in conjunction with temporary memory implemented as a circular buffer memory. The floating memory approach provides a stability of both sound and visual output at the bar graph 84. Looking momentarily at FIG. 7, the floating memory approach is illustrated. In the figure, time in milliseconds is plotted against counts in cycles per second for a probe scan which transverses over a region of higher radiation value. The random counts, c, are represented by the dashed curve which is labeled with that variable. Note that the rate increases toward the middle of the plot and decreases at either end. A floating window is continuously computed on a timed basis and is seen to have an upper edge labeled UT and a lower edge which is labeled LT. From a computed upper edge UT, a reported mean is calculated and is shown as a solid line in the figure labeled RM. It is this reported mean, RM, which is utilized to generate a sound of varying pitch which elevates as the count rate increases. To accommodate for practitioners who are tone deaf, the frequency excursions are developed from one discrete pitch step to the next. In general, the pitch varies from 300 Hz to 1200 Hz. The same reported mean, RM, is used to drive the bar graph 84. It may be observed that the vertical width of the window defined between UT and LT in FIG. 7 varies in correspondence with the count rate level.

Returning to FIG. 6C, line 676 reappears leading to the query posed at block 678 determining whether the background button or switch 48 has been depressed. In the event that it has not, then the program continues as represented at line 680. In the event of an affirmative determination, as represented at line 682 and block 684, the background count icon 96 is intermittently energized or flashed and, as represented at line 686 and block 688, the ILM background routine is called. Further, bar graph 84 is energized in accordance with the amount of time required to achieve a background count. In order to expedite the interval for counting, the background count is developed from a predetermined number of count data points representing a corresponding confidence level. Thus, where a higher count frequency is witnessed, the background count will be achieved in a relatively shorter interval of time, for example, less than a maximum interval of six seconds. Bar graph 84 will fill by sequentially energizing the LED segments thereof from 86 to 87 in a predicted time interval. However, the interval for filling the bar chart and developing background count is bounded by a minimum interval of two seconds and a maximum interval of six seconds. The program then continues as represented at line 690 and block 692 whereupon the developed background count is displayed at the character location 92 shown in FIG. 2. That display is present for the limited time interval of five seconds. At the termination of five seconds, as represented at line 694 and block 696, the flashing of the background icon 96 is terminated and, as represented at lines 698 and 680, the program continues.

In general, the "cumulative" or running ILM count rate is published at display location 80. That count rate is developed from circular memory and is updated each one half second.

Line 680 is seen to be directed to the query posed at block 700 where a determination is made as to whether the target count button 46 has been depressed. It may be recalled that this actuation is one requiring the operator to hold button 46 down for one second. In the event of a negative determination, the program continues as represented at line 702. In the event of an affirmative determination at block 700, then as represented by line 704 and block 706, the target icon 82 is intermittently energized or flashed and, as represented at line 708 and block 710 the ILM target count routine is called. Further, the bar graph 84 is filled utilizing the bounded predictive technique described in connection with block 692. When the target count has been developed, then as represented at line 712 and block 714, the target count is displayed at location 80 as seen in FIG. 2 for the finite interval limited to five seconds. The program then continues as represented at line 716 and block 718 to terminate the flashing icon 82 at the termination of the noted five seconds. The program then continues as represented at lines 720 and 702. The program next proceeds to determine whether the mute button 50 has been pressed as represented at block 722. In the event the mute button 50 has not been actuated, then the program continues as represented at line 724. However, where the button has been pressed, then as represented at line 726 and block 728 the mute icon 94 is energized intermittently or flashed and the program continues, as represented at line 730 and block 732, wherein the dynamic pitch count output for the ILM program is turned off. However, an aural feedback "beep" is maintained for any switch actuation. The program then continues as represented at lines 734 and 724.

The program next proceeds to the query posed at block 736 wherein a determination as to whether any of the buttons or switches of the range switch array 60 have been pushed or actuated. In the event they have not, then the program continues as represented at line 738. In the presence of an affirmative to that query, determination then as represented at line 740 and block 742 the dynamic pitch or sound output for the ILM program is altered to provide full scale output for the range selected. This same change is made with respect to the operation of bar graph 84. This alteration also accommodates for any initial threshold value and background value. In particular, typically a 2% threshold is invoked for each of the ranges represented at the switch array 60. Next, as represented at line 744 and block 746, the pertinent range display is illuminated. These displays are shown in FIG. 2 at 66–69. The program then continues, as represented at lines 748 and 738, to the query posed at block 750 wherein a determination is made as to whether the mode switch or button 54 has been actuated. In the event that it has, then as represented at line 752 and block 754, the program enters the RIGS mode and, as represented at line 756 and block 758, the RIGS mode display 56 is illuminated. The program then returns, as represented by line 760, to line 540 at FIG. 6A. Where the inquiry at block 750 results in a negative determination. when as represented at loop line 762, the program returns to line 676.

Figure 7:
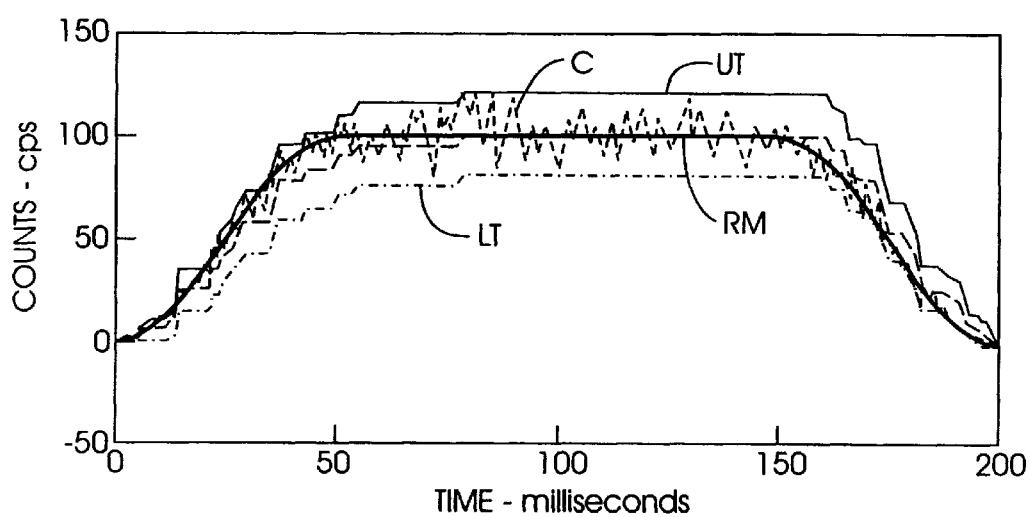
FIG. 7 is a graph illustrating the performance of a floating window form of LIM count evaluation.

In FIG. 6A at block 474, the main program activates the ILM scanning algorithm, an algorithm which initially has been described in connection with FIG. 7. In effect, a floating window is evolved having upper and lower edges, the relative positions which are calculated and from which a reported mean count value is developed. That reported mean, when converted to a count rate then is used to update a variable pitch audible output as well as the bar graph 84.

Figure 8A:
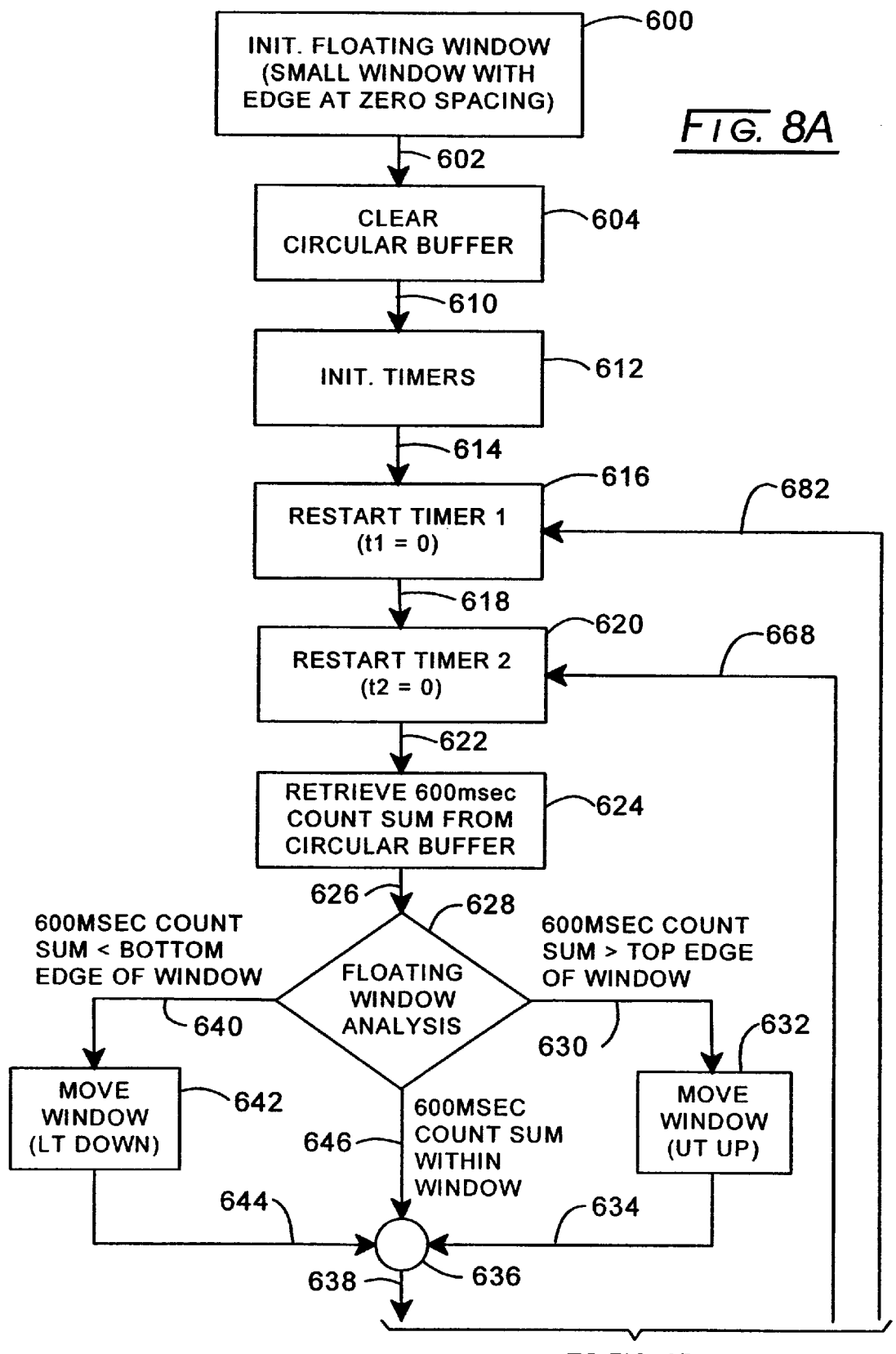
FIGS. 8A–8B combine as labeled thereon to illustrate a scanning program according to the invention.
Figure 9:
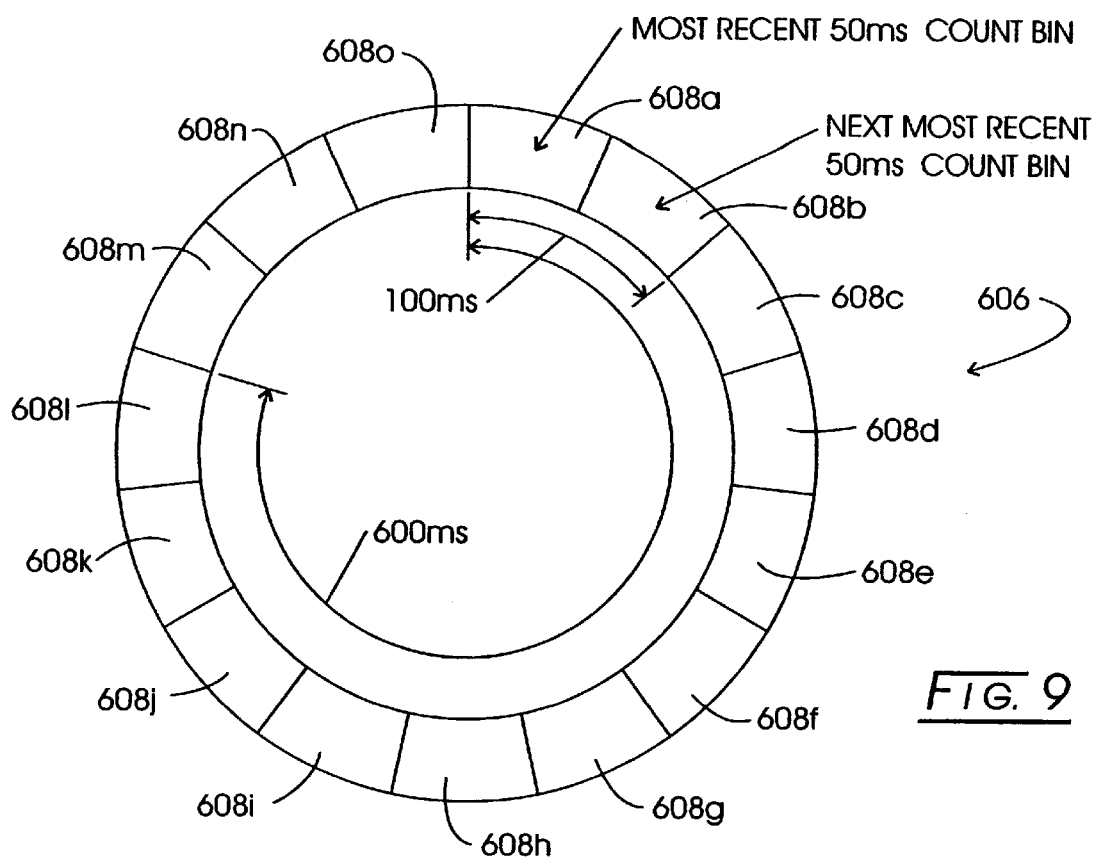
FIG. 9 is a schematic illustration of a circular buffer memory employed with the program of FIGS. 8A and 8B.

Referring to FIG. 8A, this program commences as represented at block 600 with an initialization of the floating window variable, in particular, the window commences in small width or size, the bottom edge of which is given a zero count evaluation. The program then continues as represented at line 602 and block 604 to clear a temporary memory implemented as a circular buffer memory. Looking momentarily at FIG. 9, a stylized representation of a circular buffer memory is represented in general at 606. In the course of scanning with a probe as at 12, or other probes, the program will collect valid counts or pulses within a sequence of scan intervals. These scan intervals preferably are consecutive 50 millisecond intervals. In this regard, the memory 606 is seen to have 15 memory segments identified at 608a–608o. For each of the 50 ms scans, a count sum is placed in temporary memory and with each succeeding scan interval, the count sum data is shifted. For example, the count sum maintained within bin 608a moves to bin 608b to become the next previous memory segment count value. As this occurs, the count sum value in the 15$^{th}$ bin at 608o is discarded. In developing the window definition for each 50 ms interval, count values for 12 memory segments are summed and those values are compared with the then existing window edges. Twelve such segments will amount to an accumulation of counts over an interval of 600 ms.

Returning to FIG. 8A, upon the clearing of the circular buffer, then as represented at line 610 and block 612 two timer functions are initiated and the program continues as represented at line 614 and block 616. At block 616, a timer, t1, is set to zero and started or restarted, depending upon the state of the program. This timer is associated with updating the display location 80 which occurs each 500 ms. The program then proceeds as represented at line 618 and block 620 to start or restart a second timing function, t2. This is a scan interval timer the duration of such scans preferably being 50 ms as discussed in connection with FIG. 9. Then, as represented at line 622 and block 624, the program retrieves twelve memory segment count values or count sums from the circular buffer. In particular, this will represent the most recent 600 ms values as labeled in FIG. 9. The program then continues as represented at line 626 and block 628 wherein a floating window analysis is undertaken. As represented at line 630 and block 632, where the count sum value represented by a combination of the segment count values, preferably the noted initial 600 ms combination exceeds the then existing value corresponding with the top edge of the floating window, then, as represented at block 632, the window upper edge, UT, and the window lower edge, LT, are moved upwardly by a computed amount. The program then continues as represented by line 634 node 636 and line 638.

Returning to block 628, as represented at line 640 and block 642, when the combined count sum combination of the predetermined number of segments, for example the noted 600 ms combination from bins 608a through 608l, is less than a count value representing the bottom edge of the window then the window is moved and, in particular. the lower edge, LT, and the upper edge, UT, are moved down by computed amounts. The program then continues as represented at line 644, node 636 and line 638.

Returning to block 628, where the predetermined count sum from the noted twelve memory segments falls within the window, i.e. between the upper edge, UT, and the lower edge, LT, then as represented at line 646, no window alteration occurs and, in effect, the reported output will be maintained in a stable condition.

For the condition represented at line 630 and block 632, where the 700 ms count sum (CS) is greater than the value of the upper edge, UT, then the following expressions are implemented:

$$UT = CS \tag{1}$$

$$RM = \left( \frac{-FWF}{2} + \frac{\sqrt{FWF^2 + 4 \cdot CS}}{2} \right)^2 \tag{2}$$

$$LT = RM - FWF \cdot \sqrt{RM} \tag{3}$$

Where
UT is the count sum corresponding with the upper edge of the window

CS is count sum for a count period
T is count period i.e., 600 ms
RM is reported mean
FWF is a floating window factor corresponding with a number of statistical standard deviations or sigmas
LT is the count sum corresponding with the lower edge of the window.

Where the condition represented at line 640 and block 642 obtains, then the count sum CS, is less than the lower edge, LT, and the following expressions are implemented:

$$LT = CS \tag{4}$$

$$RM = \left( \frac{-FWF}{2} - \frac{\sqrt{FWF^2 + 4 \cdot CS}}{2} \right)^2 \tag{5}$$

$$UT = RM + FWF \cdot \sqrt{RM} \tag{6}$$

From the reported mean, RM, derived above, a count rate in counts per second, referred to as the "Acquired Count Rate ILM Value" (ACRIV) is computed as follows:

$$ACRIV = RM/T \tag{7}$$

For startup conditions, i.e., a first pass within the routine, the initialization discussed in connection with block 100 provides that UT=1.0, LT=1.0, RM=0, FWF=2.0, and T=600 ms. The window defining expressions set forth above were evolved following a study of the attributes of gamma radiation which tends to emulate Poisson distributions.

Figure 8B:
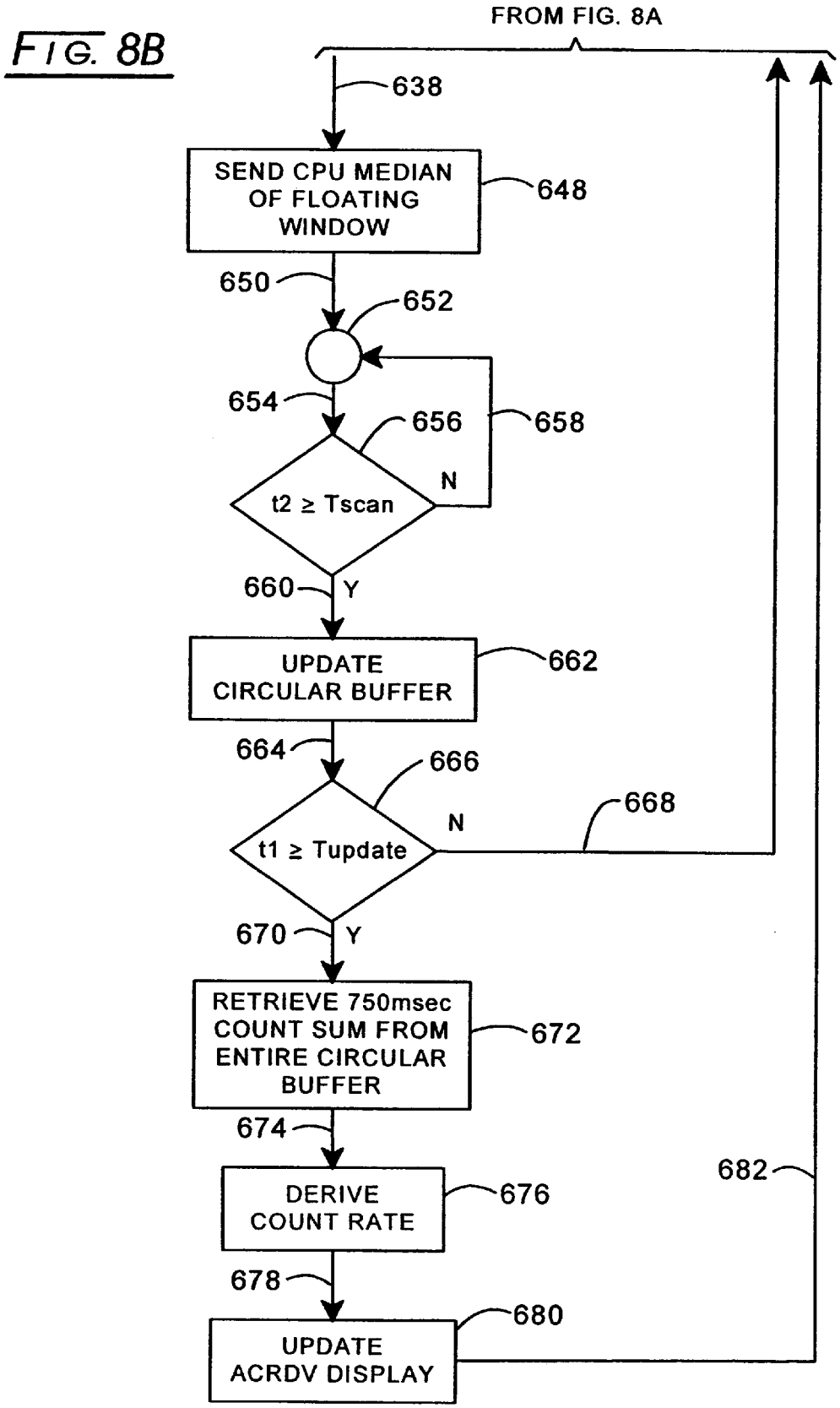

Looking to FIG. 8B, line 638 is seen to reappear, extending to block 648 where the program sends the central processor control 232 the mean count rate of the floating window as developed in connection with expression (7) above. The program then continues as represented at line 650 and, node 652 and line 654 to the query posed at block 656. At that position, a determination is made as whether the time, t2, has equaled or exceeded the scan interval, Tscan, i.e., 50 ms. In the event that it has not, then the program dwells as represented by loop line 658. At the termination of a scan interval, then as represented at line 660 and block 662, the count sum is inserted in the circular buffer, for example at bin 608a as described in connection with FIG. 9. Then, as represented at line 664 and block 666, a query is made as to whether the timer, t1 has timed out the update interval, Tupdate. This interval may, for example, be 500 ms. In the event that timeout has not occurred then, as represented at line 668, the program loops to block 620 in FIG. 8A providing for the restart of timing function, t2. Where the update interval has occurred, then as represented at line 670 and block 672, the program retrieves the accumulative value of the entire circular buffer memory which represents fifteen bins and an accumulation of segment count values representing a 750 ms interval of scanning. Recall that this retrieval occurs each 500 ms. The program then continues as represented at line 674 and block 676 to derive count rate by dividing the count sum retrieved in connection with block 672 by 750 ms. The program then continues as represented at line 678 and block 680 to update the count rate display at location 80 in window 42. The count rate value is referred to as: "Acquired Count Rate Display Value" (ACRDV). Upon updating the display at location 80 the program returns to block 616 shown in FIG. 8A as represented by loop line 682.

It is generally desirable to carry out medical/surgical procedures with reasonable rapidity. For procedures involving the instant ILM mode of performance of the system of the invention, the intervals for developing background count rates and target count rates as discussed at respective blocks 678 and 700 in connection with FIG. 8C can be advantageously diminished in many instances. In this regard, the Acquired Count Rate Value (ACRV) for these procedures can be analyzed in terms of a confidence interval or confidence level analysis. The procedure is one wherein upper and lower time bounds are predetermined. In this regard, for developing the target count or background count, the count evaluation will occur in a minimum interval of two seconds and in a maximum interval of 6 seconds. Additionally, the requisite counting interval is determined in a predictive sense upon the acquisition of, n, valid counts or data points. For the application at hand, that component, n, has been established at 100.

Figure 10:
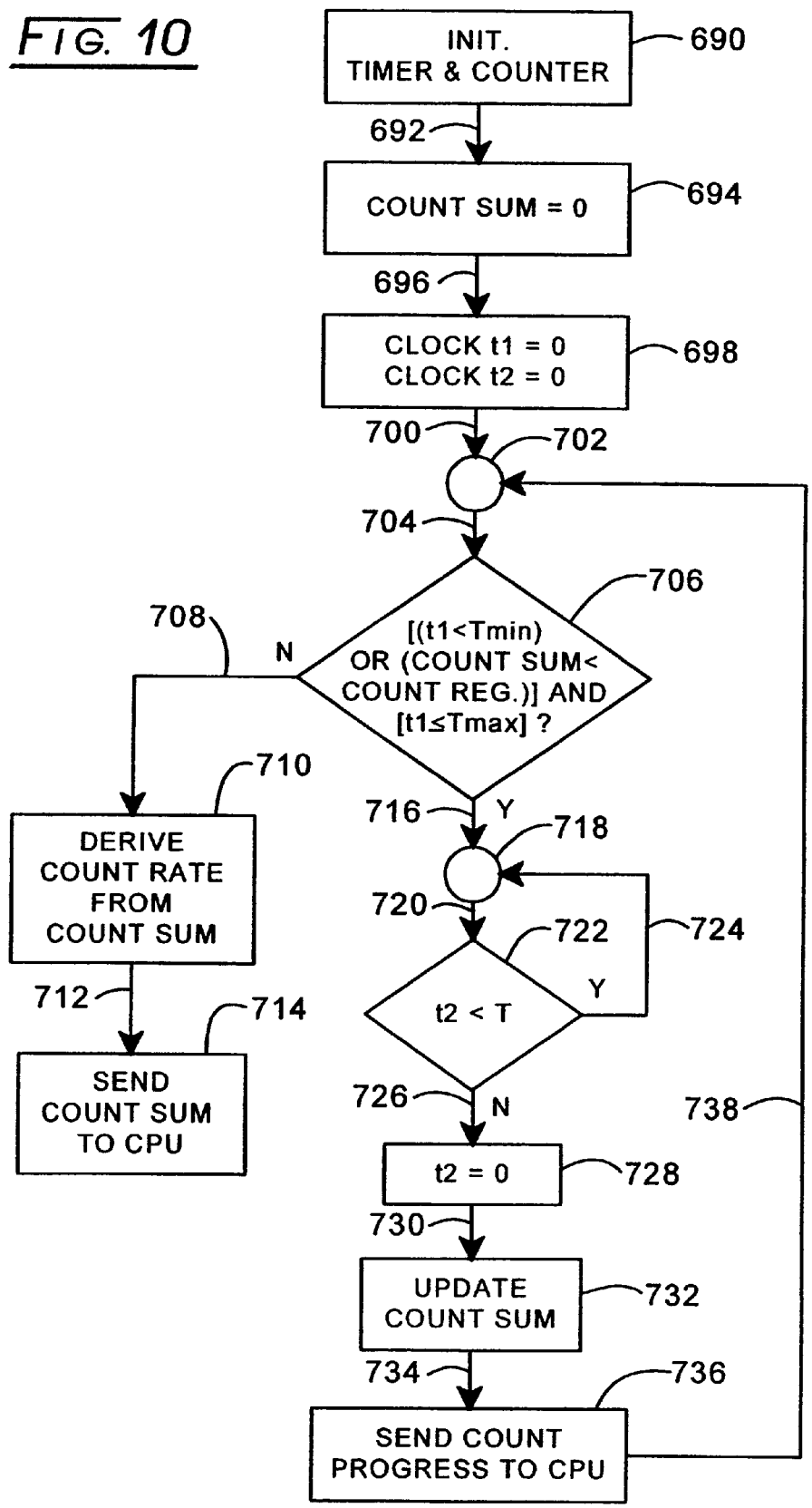
FIG. 10 is a flow chart describing a bounded predictive data compilation technique of the inventor.

Looking to FIG. 10, a flow chart describing this program, which sometimes has been referred to as "Hybrid Delta T" is set forth. The program commences at block 690 wherein two timer functions and a counter function are initialized. Then, as represented at line 692 and block 694, the counter function is designated as having a count sum of 0. As represented at line 696 and block 698, two clocks, t1, and t2 are set to 0, and in effect, started, while a cumulative count of validated photon event related pulses is undertaken. The clock, t2, provides an updating interval, while the clock, t1, is a running clock representing elapsed time for the target count or background procedure. The program then progresses as represented at line 700, node 702 and line 704 to the bounding and data point evaluation logic represented at block 706. It is at this conjuncture that the logic for developing the enhanced timing is carried out. The query determines whether elapsed time, t1, is less than a minimum time, Tmin. Tmin, for the embodiment at hand, is established at 2 seconds and this is the lower bound in time. This first expression is logically ORed with the condition that the cumulative number of counts thus far counted is less than the counts required, i.e., the value of the, n. As noted above, for the instant application, this value is 100. The above ORed conditions then are ANDed logically with the condition that the accumulative time, t1, be less than or equal to the upper bound in time, Tmax. For the instant embodiment, Tmax is set at 6 seconds. That upper bound evolves from experience with the surgical profession. Where the conditions of block 706 are not present, then adequate data will have been derived and, as represented at line 708 and block 710 the count rate is derived from the cumulative count sum of the counter by dividing the latter value by elapsed time, t1. This data, representing count rate for either background or target count, is then conveyed to the central processor control 232 as represented at lines 712 and block 714.

However, in the event of an affirmative determination with respect to the logic as set forth at block 706, then sufficient data has not been collected, the lower bound may not have been reached or the upper bound has not been reached. In the presence of such conditions, then as represented at line 716, node 718 and line 720, the program queries as to whether the timer, t2, is less than an update time, T. For the present embodiment, this update time, T, is set at 50 ms. This query is posed at block 722. In the event of an affirmative determination, the program dwells as represented by loop line 724. In the event of a negative determination with respect to the query posed at block 722, then the update time interval has occurred and, as represented at line 726 and block 728 the update timer is set to 0 and, as represented at line 730 and block 732, the count sum or cumulative amount as number of counts thus far counted is updated and is represented at line 734 and block 736, a count progress report is sent to the central processor control 232. With such input to this control, the number of segments from first at 86 toward the last at 87 of bar graph 84 is established predictably to apprise the practitioner of the amount of time thus far expended in the target count or background procedure and the amount of time still required to complete it. The program then returns as represented at loop line 738 extending to node 702.

Figure 11:
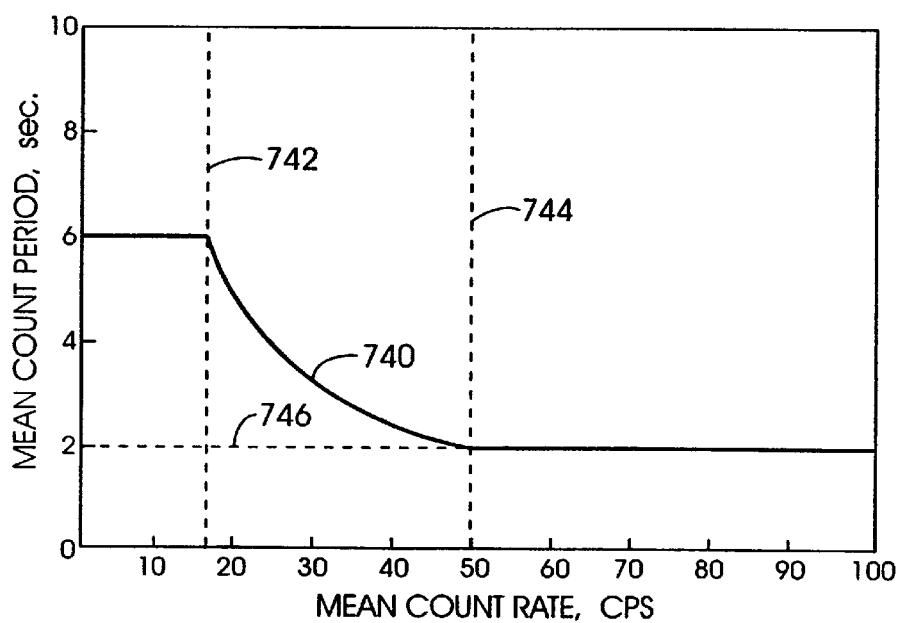
FIG. 11 is a graph plotting mean count period vs. mean count rate.

Referring to FIG. 11, a curve 740 is provided which describes the performance of the instant algorithm with respect to mean count period in seconds and mean count rate in counts per second. Curve 740 is seen to plateau at the upper bound of 6 seconds up to a count rate of 16.7 CPS as represented at the dashed line 742. As is apparent, 100 data points will be achieved at a mean count rate of 50 CPS as represented at dashed lines 744 and 746. Intermediate the noted dashed lines, the predictive performance of the algorithm is displayed representing a variable time interval of 4 seconds during which the bar graph 84 at window 42 will be filled. For example, FIG. 11 shows that at a mean count rate of about 26 CPS about 4 seconds will be required to fill the bar graph 84.

Studies of the instant system has shown that there is a 95% probability that the value derived for target count or background count is going to be within ±19.8% of true mean. In this regard, to solve for the confidence interval, the confidence level, P, is set equal to the integral of the probability mask function across the confidence interval, b. In this regard, reference is made to expression $$P = \sum_{(1-b)n}^{(1+b)n} \frac{e^{-\lambda}\lambda^n}{n!} d\lambda \qquad (8)$$

In the above expression the measured count sum is represented by, n, and the true mean count sum is represented by lambda.

Substituting the appropriate values into expression (8), the following expression obtains:

$$0.95 = \int_{(1-b)100}^{(1+b)100} \frac{e^{-\lambda}\lambda^{100}}{100!} d\lambda \qquad (9)$$

The solution for expression (9) yields b=0.198, or in other words, the 95% confidence interval is 19.8% for the measured count sum.

Since certain changes may be made in the above described system, apparatus, and method without departing from the scope of the invention herein involved, it is intended that all matter contained in the description thereof or shown in the accompanying drawings shall be interpreted as illustrative and not in a limiting sense.

What is claimed is:

1. A system for detecting and locating sources of radiation at a region of interest, comprising:

a probe moveable within said region of interest to provide a pulsed output corresponding with radiation from said source;

a readout responsive to a readout input for providing a perceptive output;

a signal treatment network responsive to validate said pulsed outputs to provide count signals;

a control circuit including circular memory having bins from first to last for retaining memory segment count values, responsive to said count signals during consecutive scan intervals to derive corresponding successive count values for retention as said memory segment count values, responsive with respect to a given said scan interval to compare the count sum value, CS, represented by a predetermined number of said memory segment count values derived over a count period, T, with a window defining upper edge value, UT, said window having a lower edge value, LT, responsive when said count sum, CS, is greater than said upper edge value, UT, to adjust said window in accordance with the expressions:

$$UT = CS,$$

$$RM = \left(\frac{-FWF}{2} + \frac{\sqrt{FWF^2 + 4 \cdot CS}}{2}\right)^2, \text{ and}$$

$$LT = RM - FWF \cdot \sqrt{RM},$$

where RM is reported mean and FWF is a statistically significant floating window factor, responsive when said count sum, CS, is less than said lower edge value, LT, to adjust said window in accordance with the expressions:

$$LT = CS,$$

$$RM = \left(\frac{-FWF}{2} - \frac{\sqrt{FWF^2 + 4 \cdot CS}}{2}\right)^2,$$

$$UT = RM + FWF \cdot \sqrt{RM},$$

and responsive to provide said readout input in correspondence with the expression:

RM/T.

2. The system of claim 1 in which said floating window factor has a value of about two.

3. The system of claim 2 in which:

each said scan interval is 50 milliseconds in duration; and said count period, T, is 600 milliseconds.

4. The system of claim 1 in which said count sum, CS, is the sum of a predetermined number of said memory segment count values within said memory bins commencing with said first memory bin.

5. The system of claim 1 in which:

said readout includes a visually perspective bar graph output with segments energizable from first to last in response to said readout input.

6. The system of claim 1 in which said readout provides said perceptive output as an audible sound having a frequency corresponding with the output count rate value represented by said readout input.

7. The system of claim 1 including:

a visual display assembly responsive to a count rate signal to derive a numerical count rate output; and said control circuit is responsive at the timeout of successive update intervals to access a select number of successive said memory segment count values corresponding with an elapsed interval of timing and derive a said numerical count rate output in correspondence therewith.

8. The system of claim 7 in which:

said update interval is about 500 milliseconds; and said elapsed interval of timing is 750 milliseconds.

9. A method for detecting and locating sources of radiation at a region of interest, comprising the steps of:

(a) providing a probe moveable within said region of interest;

(b) scanning said probe within said region of interest to derive a scanned pulsed output;

(c) providing a readout responsive to a readout input for deriving a perceptive output;

(d) providing a signal treatment network responsive to validate said pulsed outputs to provide count signals;

(e) providing a control circuit including a circular memory;

(f) compiling said count signals for a sequence of scan intervals to derive corresponding successive count values for retention as memory segment count values;

(g) locating said memory segment count values in said sequence in said circular memory;

(h) accessing said circular memory and determining a count sum, CS, with respect to a given said scan interval as the sum of a predetermined number of successive said memory segment count values including that memory segment count value corresponding with said given interval, said count sum CS, having been derived over a count period, T;

(i) comparing said count sum, CS, with the upper edge, UT, and lower edge, LT, of a floating window;

(j) when said comparison of step (i) results in a condition where the value for CS is greater than the value for UT, then adjusting said floating window in accordance with the following expressions:

$$UT = CS,$$

$$RM = \left(\frac{-FWF}{2} + \frac{\sqrt{FWF^2 + 4 \cdot CS}}{2}\right)^2, \text{ and}$$

$$LT = RM - FWF \cdot \sqrt{RM},$$

where RM is reported mean and FWF is a statistically significant floating window factor;

(k) when said comparison of step (i) results in a condition where the value for CS is less than the value for LT, then adjusting said floating window in accordance with the following expressions:

$$LT = CS,$$

$$RM = \left(\frac{-FWF}{2} - \frac{\sqrt{FWF^2 + 4 \cdot CS}}{2}\right)^2,$$

$$UT = RM + FWF \cdot \sqrt{RM}; \text{ and}$$

(l) providing said readout input in correspondence with the expression:

RM/T.

10. The method of claim 9 in which said floating window factor, FWF, has a value of about two.

11. The method of claim 9 in which said step (i) provides said readout as a visually perceptible bar graph with segments energizable from first to last in response to said readout input.

12. The method of claim 9 in which said step (i) provides said readout as an aurally perceptive sound having a frequency corresponding with the count rate value represented by said readout input.

13. The method of claim 9 in which:

said scan intervals of step (f) are about 50 milliseconds; and said count period, T, of step (h) is about 600 milliseconds.

14. The method of claim 9 including the steps of:

(m) providing a visual display assembly responsive to a count rate signal to derive a numerical count rate output;

(n) accessing a select number of successive said memory segment count values corresponding with an elapsed interval of time and deriving said numerical count rate output in correspondence therewith for a sequence of update intervals.

15. The method of claim 14 in which:

said update interval of step (n) is about 500 milliseconds; and said elapsed interval of step (n) is about 750 milliseconds.

16. A system for detecting and locating sources of radiation at a region of interest, comprising:

a probe moveable within said region of interest to provide a pulsed output corresponding with radiation from said source;

a readout responsive to a readout input for providing a perceptive output;

a signal treatment network responsive to validate said pulse outputs to provide count signals;

a control circuit including temporary memory for retaining memory segment count values, responsive to said count signals during consecutive scan intervals to derive corresponding successive count values for retention as said memory segment count values, responsive with respect to a given said scan interval to compare the count sum value represented by a predetermined combination of said segment count values with window defining upper and lower edge values representing count sums, responsive to move said window defining edge values a computed amount when said compared count sum value is greater than said window defining upper value, responsive to provide said readout input in correspondence with an output count rate value derived with respect to a count sum intermediate said window defining values subsequent to said comparison.

17. The system of claim 16 in which each said scan interval is about 50 milliseconds in duration.

18. The system of claim 17 in which said predetermined combination of said segment count values represents count values corresponding to about 12 said scan intervals.

19. The system of claim 16 in which said readout provides said perceptive output as an audible sound having a frequency corresponding with the output count rate value represented by said readout input.

20. The system of claim 16 in which said readout provides said perceptive output as a visually perceptive bar graph output with segments energizable from first-to-last in correspondence with the output count rate value represented by said readout input.

21. The system of claim 16 in which:

said temporary memory is a circular buffer memory having a predetermined number of memory segments for retaining segment count values corresponding with count signals occurring during a scan interval;

said readout includes a visually perceptive readout responsive to a said readout input representing a count rate signal to display a count rate value; and said control circuit is responsive at the timeout of successive update intervals to access a select number of said memory segments and derive said readout input representing a count rate signal corresponding with the cumulative count value of said select number of memory segments.

22. The system of claim 21 in which said select number of memory segments is 15.

23. The system of claim 21 wherein:

said region of interest is within an environment evidencing background radiation;

including a background switch actuable to provide a background actuation signal;

said probe being positionable to evaluate said background radiation and derive a background pulsed output corresponding therewith;

said signal treatment network is responsive to validate said background pulse output to provide background count signals; and said control circuit is responsive to said background actuation signal and to said background count signals to derive a background count rate value, and derives a said readout input for providing an aurally perceptive output only when said output count rate value is greater than said background count rate value.

24. The system of claim 21 in which said signal treatment network comprises:

an energy window network including a lower threshold operational amplifier having a lower threshold reference value and responsive to said pulsed output to validate the minimum energy values thereof; and a pulse width discriminator for validating only those pulse outputs which have pulse widths below a pulse width value representing noise.

25. The system of claim 24 in which said pulse width discriminator derives said pulse widths for validation in correspondence with said lower threshold reference value.

26. A system for evaluating a source of radiation at a location of interest, comprising:

a probe having a detector positionable adjacent said location having a pulsed output corresponding with radiation impinging thereon from said source;

a signal treatment circuit responsive to validate said pulsed output to provide count signals;

a readout responsive to a readout input for providing a visually perceptive output;

a control circuit responsive to count said count signals for each of a succession of count intervals of predetermined duration and deriving a cumulative count sum at the termination of each said count interval, responsive to carry out said count for at least a lower bound interval of time, $T_{min}$, and not longer than the termination of that terminating count interval during which upper bound total count time limit, $T_{max}$, occurs, further responsive to a cumulative count sum upper bound to terminate said count at the termination of that terminating count interval within which said count sum upper bound is reached, further responsive to derive a count rate value with respect to said cumulative count sum and the cumulative time duration of said count intervals through said terminating count interval, and responsive to derive said readout input in correspondence with said count rate value.

27. The system of claim 26 in which said count interval is of fixed duration, and said total count time, $T_{max}$, is an integer multiple of said count interval fixed duration.

28. The system of claim 26 in which said control circuit is responsive to derive said readout input for a finite display interval.

29. The system of claim 26 in which:
said readout includes a bar graph with segments energizable from first-to-last in response to a sequence of count duration graphics signals;
said control circuit is responsive to derive an updating count sum signal at the termination of each said count interval and to derive a said count duration graphics signal corresponding therewith.

30. The system of claim 29 in which each said count duration graphics signal is derived by said control circuit in correspondence with the difference between said cumulative count sum and said cumulative count sum upper bound.

31. The system of claim 30 in which each said count duration graphics signal is derived by said control circuit in correspondence with said lower bound interval when said cumulative count equals said cumulative count upper bound before the termination of said lower bound interval.

32. The system of claim 31 in which each said count duration graphics signal is derived by said control circuit in correspondence with the said time to termination of that terminating count interval occurring for which an upper bound total count time limit, $T_{max}$, occurs, when said cumulative count sum will not equal said cumulative count sum upper bound within said total count time limit, $T_{max}$.

33. The system of claim 26 in which said lower bound interval is about two seconds or less.

34. The system of claim 26 in which said total count time limit is about six seconds.

35. The system of claim 26 in which each said count interval is about 50 milliseconds.

36. The system of claim 26 including:
a target count switch actuable to derive a target mode signal;
said readout includes a target icon assembly energizable in response to said readout input to provide a visually perceptible target icon display; and
said control circuit is responsive in the presence of said target mode signal to derive said readout input throughout said accumulative time duration of said count intervals through said terminating count interval.

37. The system of claim 36 in which said control circuit derives said readout input intermittently in the presence of said target mode signal.

38. The system of claim 36 including:
a background switch actuable to derive a background mode signal;
said readout includes a background icon assembly energizable in response to said readout input to provide a visually perceptible background icon display; and
said control circuit is responsive in the presence of said background mode signal to derive said readout input throughout said accumulative time duration of said count intervals through said terminating count interval.

39. The system of claim 38 in which said control circuit derives said readout input intermittently in the presence of said background mode signal.

* * * * *